United States Patent
Diduch et al.

(10) Patent No.: US 7,842,050 B2
(45) Date of Patent: Nov. 30, 2010

(54) SUTURE PASSING DEVICES

(76) Inventors: David R. Diduch, 1560 Old Oaks Dr., Charlottesville, VA (US) 22902; James G. Whayne, 137 New Castle Dr., Chapel Hill, NC (US) 27517

(*) Notice: Subject to any disclaimer, the term of this patent is extended or adjusted under 35 U.S.C. 154(b) by 217 days.

(21) Appl. No.: 10/084,283

(22) Filed: Feb. 26, 2002

(65) Prior Publication Data

US 2002/0147456 A1 Oct. 10, 2002

Related U.S. Application Data

(60) Provisional application No. 60/313,779, filed on Aug. 20, 2001, provisional application No. 60/271,392, filed on Feb. 26, 2001.

(51) Int. Cl.
*A61B 17/04* (2006.01)
*A61B 17/10* (2006.01)

(52) U.S. Cl. ........................ 606/148; 606/222

(58) Field of Classification Search ......... 606/135–149, 606/222–233, 1, 78, 110, 113, 114, 117, 606/178, 167, 150, 205, 207; 604/272
See application file for complete search history.

(56) References Cited

U.S. PATENT DOCUMENTS

| | | | |
|---|---|---|---|
| 1,815,725 A | 7/1931 | Pilling et al. | |
| 3,470,875 A | 10/1969 | Johnson | |
| 3,842,840 A | 10/1974 | Schweizer | |
| 3,946,740 A | 3/1976 | Bassett | |
| 4,164,225 A | 8/1979 | Johnson et al. | |
| 4,312,337 A | 1/1982 | Donohue | |
| 4,491,135 A * | 1/1985 | Klein | 606/147 |
| 4,493,323 A | 1/1985 | Albright et al. | |
| 4,596,249 A | 6/1986 | Freda et al. | |
| 4,602,635 A | 7/1986 | Mulhollan et al. | |
| 4,621,640 A | 11/1986 | Mulhollan et al. | |
| 4,836,205 A * | 6/1989 | Barrett | 606/144 |
| 4,890,615 A | 1/1990 | Caspari et al. | |
| 4,923,461 A | 5/1990 | Caspari et al. | |
| 4,926,860 A | 5/1990 | Stice et al. | |

(Continued)

FOREIGN PATENT DOCUMENTS

EP 0812572 A1 * 12/1997

OTHER PUBLICATIONS

NEEDLEPUNCH advertisement, Arthrex.

(Continued)

*Primary Examiner*—(Jackie) Tan-Uyen T Ho
*Assistant Examiner*—Jing Rui Ou
(74) *Attorney, Agent, or Firm*—Moazzam & Associates, LLC

(57) ABSTRACT

An embodiment of the invention includes a surgical device for passing suture through soft tissue. The surgical device can include at least one elongate superelastic member having a thickness and having a first resting configuration that defines at least one curve having a first radius of curvature greater than or equal to 3 times the thickness of the superelastic member. The surgical device also can include a thermally formed opening in the superelastic member, the opening adapted to receive at least one strand of suture. Moreover, the surgical device can include a superelastic member adapted to be straightened into a second configuration having a second radius of curvature larger than the first radius of curvature.

6 Claims, 17 Drawing Sheets

U.S. PATENT DOCUMENTS

| | | | |
|---|---|---|---|
| 5,059,201 A | | 10/1991 | Asnis |
| 5,342,389 A | * | 8/1994 | Haber et al. ............... 606/205 |
| 5,382,258 A | * | 1/1995 | Chow ........................ 606/148 |
| 5,607,435 A | * | 3/1997 | Sachdeva et al. ............ 606/139 |
| 5,702,407 A | * | 12/1997 | Kaji .......................... 606/139 |
| 5,713,908 A | * | 2/1998 | Jameel et al. ............... 606/148 |
| 5,749,879 A | * | 5/1998 | Middleman et al. ......... 606/139 |
| 5,797,961 A | * | 8/1998 | Smith et al. ................. 606/222 |
| 5,820,628 A | * | 10/1998 | Middleman et al. ......... 606/147 |
| 5,868,760 A | * | 2/1999 | McGuckin, Jr. ............. 606/139 |
| 5,947,982 A | | 9/1999 | Duran |
| 5,980,538 A | * | 11/1999 | Fuchs et al. ................ 606/145 |
| 6,077,277 A | * | 6/2000 | Mollenauer et al. ......... 606/144 |
| 6,533,795 B1 | | 3/2003 | Tran et al. |
| 7,112,208 B2 | * | 9/2006 | Morris et al. ............... 606/144 |
| 2002/0103493 A1 | * | 8/2002 | Thal .......................... 606/144 |
| 2004/0249394 A1 | * | 12/2004 | Morris et al. ............... 606/144 |
| 2006/0020273 A1 | | 1/2006 | Hatch et al. |

OTHER PUBLICATIONS

The ExpresSew Suture Passer advertisement, Surgical Solutions.
AnchorSew advertisement, USS Sports Medicine.
Melzer, A., Pelton, A., Superelastic Shape-Memory Technology of Nitinol in Medicine. Min Invas Ther & Allied Technol. 2000:9(2) 59-60.

* cited by examiner

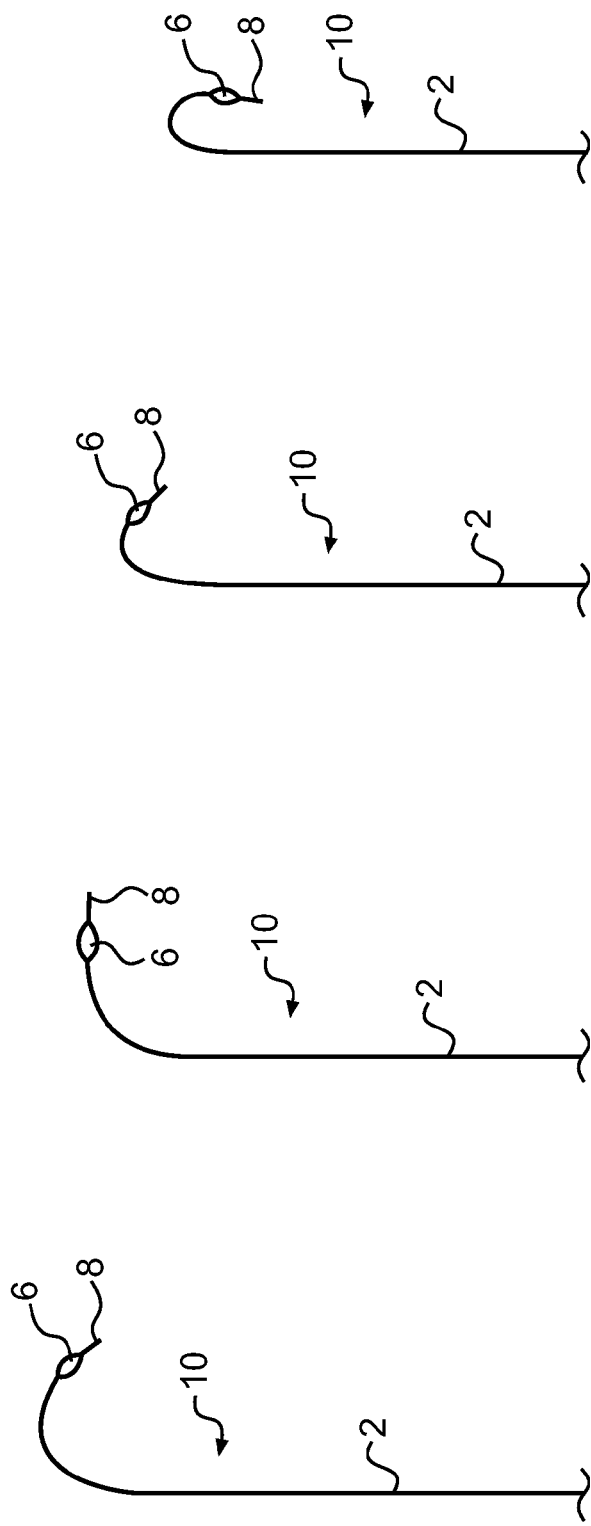

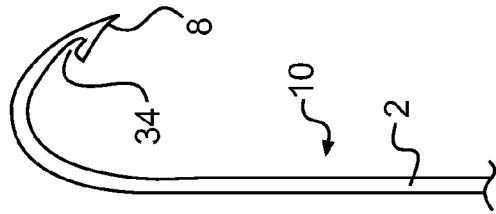
FIG. 6
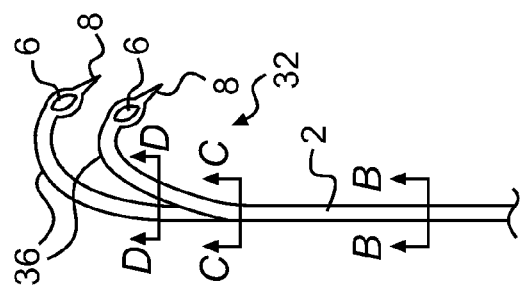
FIG. 5a
B-B FIG. 5b
C-C FIG. 5c
D-D FIG. 5d
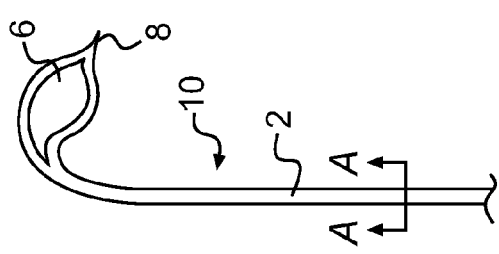
FIG. 4a
A-A FIG. 4b
A-A FIG. 4c
A-A FIG. 4d

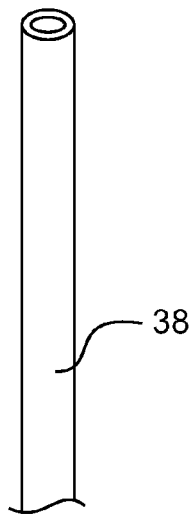 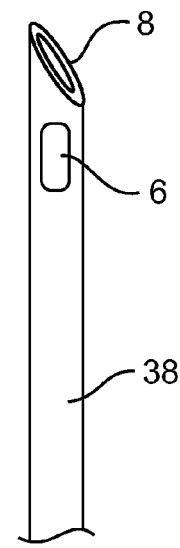
FIG. 7a  FIG. 7b
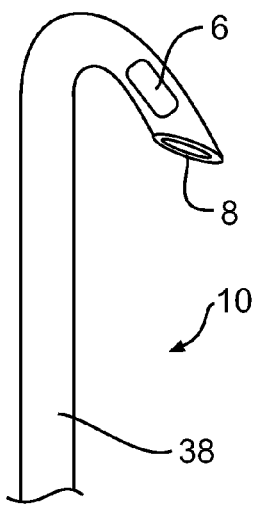 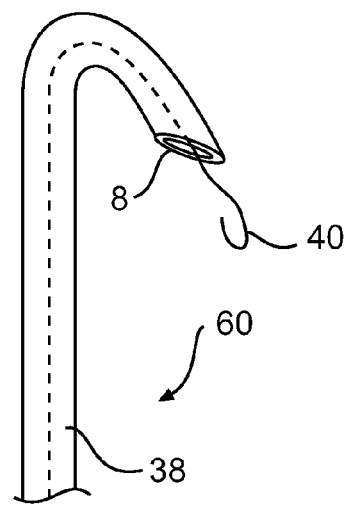
FIG. 7c  FIG. 8a

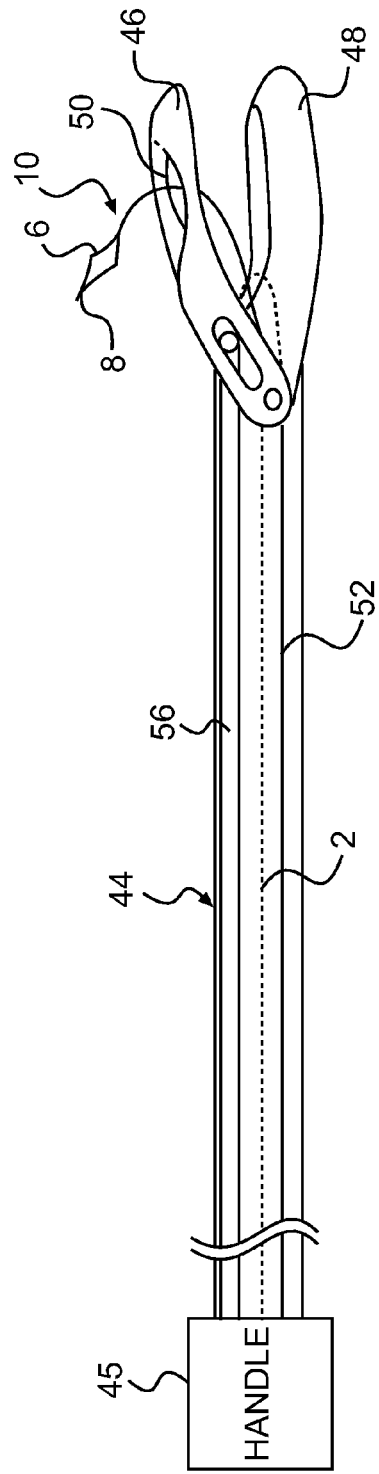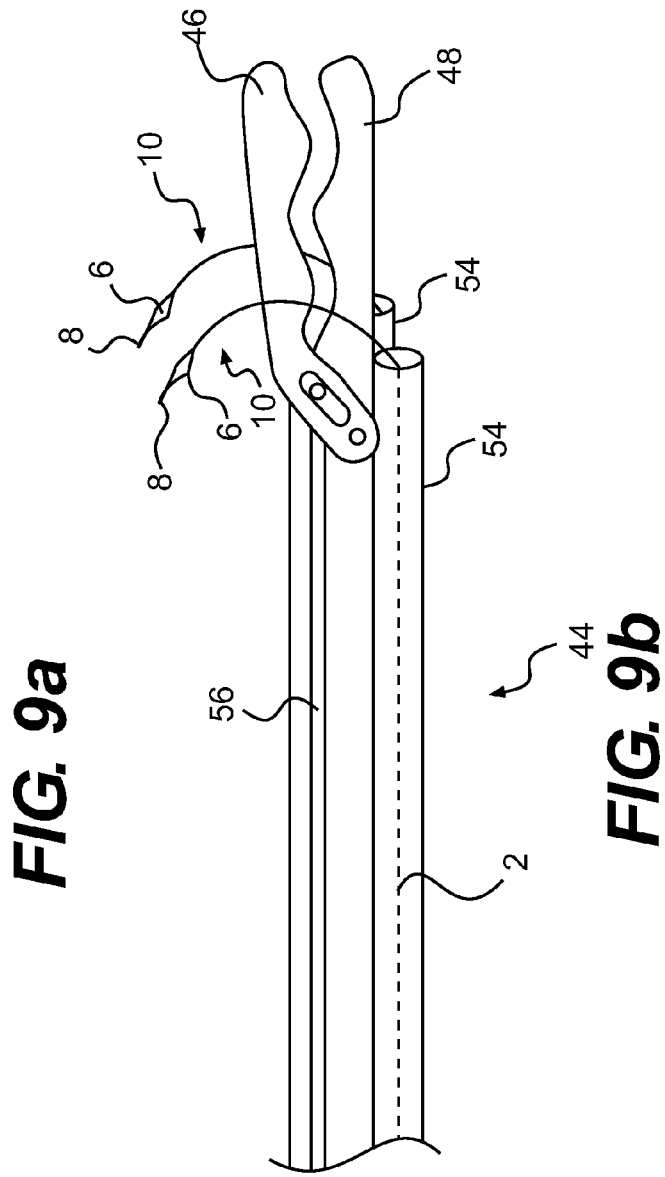
FIG. 9a
FIG. 9b

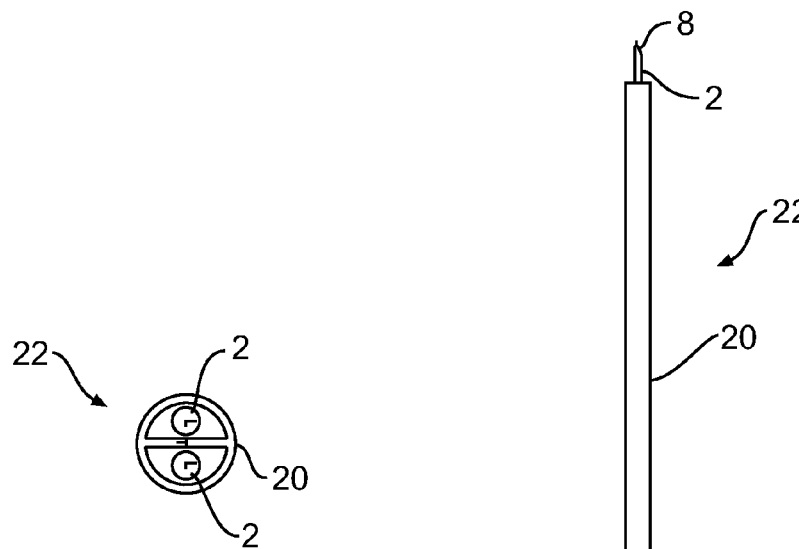
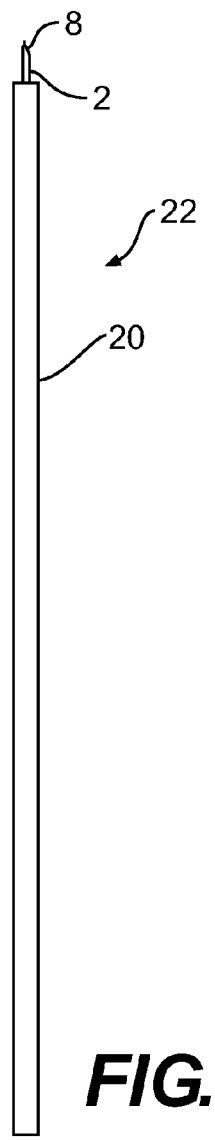
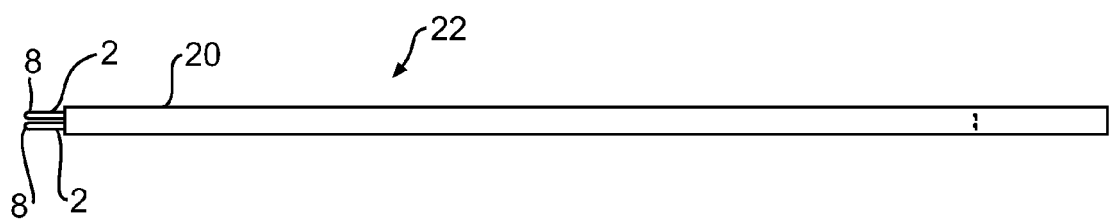
FIG. 10b
FIG. 10a
FIG. 10c

SUTURE PASSING DEVICES

CROSS-REFERENCE TO RELATED APPLICATIONS

This application is related to, claims priority to, and incorporates by reference herein in their entirety, the following U.S. patent applications:

Provisional application Ser. No. 60/271,392, filed Feb. 26, 2001 entitled "Variable Angled Needle and Suture Passer"; and Provisional application Ser. No. 60/313,779, filed Aug. 20, 2001 entitled "Superelastic Puncturing Device and Suture Passer".

FIELD OF THE INVENTIONS

Embodiments of the invention relate to devices and methods for less invasive suturing of soft tissue. More particularly, certain embodiments of the invention relate to superelastic suture passing devices capable of advancing or retracting suture strands, not integral to the puncturing component(s) of the suture passing device, through soft tissue (e.g. skin, tendons, muscles, ligaments, vascular tissue, and/or other tissue) during arthroscopic, laparoscopic, or other minimally invasive procedures. Certain embodiments of devices and methods of the invention also enable creating mattress suture attachments or other suture knots in which multiple suture strands are (simultaneously or individually) advanced or retracted through soft tissue at specific locations in order to maximize the reliability of the bond between the soft tissue and another structure (e.g. bone, muscle, other region of the soft tissue, or other anatomic structure).

DESCRIPTION OF THE RELATED ART

Arthroscopic surgery, laparoscopic surgery, and other less invasive surgical procedures require the suturing of soft tissue in an area not easily accessible due to the lack of space or direction of access to the soft tissue. Existing methods of suturing in such environments create a simple suture knot with only one suture pass through tissue due to the complexity of advancing suture in such tight access (confined) regions. A mattress suture configuration has been demonstrated as mechanically superior to single pass suturing and has a lower rate of pullout. However, passing a mattress suture (as well as a single pass suture) in less invasive procedures is exceedingly difficult and cumbersome using existing methods, which consist of rigid needles or snares that must be rotated through the soft tissue.

BRIEF DESCRIPTION OF DRAWINGS

Several exemplary embodiments of the present invention, and many features and advantages of those exemplary embodiments will be elaborated in the following detailed description and accompanying drawings, in which:

FIGS. 3a to d show side views of four superelastic puncturing component embodiments;

FIGS. 4a to d show a side view and three cross-sectional views of a superelastic puncturing component embodiment incorporating a snare;

FIGS. 5a to d show a side view and three cross-sectional views of a superelastic puncturing component embodiment incorporating two discrete distal sections;

FIG. 6 shows a side view of a superelastic puncturing component embodiment that contains a crochet hook;

FIGS. 7a to c show side views of three steps involved in fabricating a superelastic puncturing component embodiment from superelastic raw material;

FIG. 8a shows a side view of a superelastic tubular puncturing component incorporating a moveable snare;

FIGS. 10a, b, and c show a side view, an end view, and a top view of a double barrel suture passing device in a compressed, low profile configuration;

DETAILED DESCRIPTION

Figure 1A:
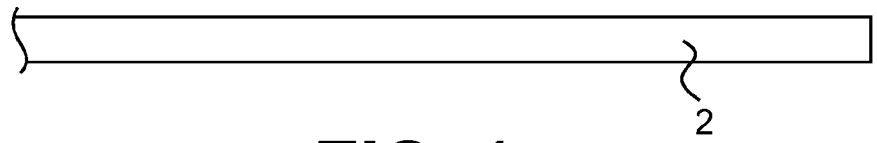
FIGS. 1a to d show side views of four steps for fabricating a superelastic puncturing component embodiment from superelastic wire, ribbon, bar or other raw material.
Figure 1B:
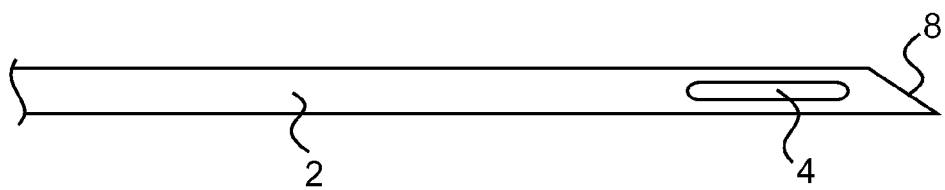

A need exists for suture passing devices and methods that enable creating mattress suture knots through soft tissue during arthroscopic or laparoscopic procedures. In addition, such devices and methods could simplify other difficult surgical procedures or any operation requiring detailed suturing in a confined or difficult to reach space. The needed technology also could enable certain procedures to be performed arthroscopically or laparoscopically through limited incisions that previously required large, open incisions with inherent morbidity and risks to other anatomic structures. Such inventive devices and methods thus could enable patients to undergo such reparative or therapeutic surgical procedures while enduring less pain, expedited hospital stays, and shorter rehabilitative and recovery times.

The present invention relates to methods and devices that enable passing sharpened puncturing components of a suture passing device(s), and suture (one, two, or multiple strands) through soft tissue during less invasive procedures. To accomplish this, the suture passing devices (which can advance, retract, and/or snare suture strands) incorporate superelastic puncturing components that exhibit superelastic properties such that they can be compressed into a straightening tube or integrated lumen of a device having a substantially smaller profile during deployment. The superelastic puncturing components of the suture passing devices return towards their preformed, resting, enlarged shape upon removal of the compressive forces required to reduce their profiles thereby enabling the advancement or retraction of one or more sutures through soft tissue despite limited access to the soft tissue, characteristic of less invasive procedures. Another requirement of the superelastic puncturing components of the suture passing devices is an integral keyhole, eyelet opening or crochet hook capable of advancing and/or retracting suture strands coincident with manipulations of the puncturing devices.

Embodiments of the present invention can provide suture passing devices fabricated with superelastic puncturing components or snares that enable advancing or retracting suture through soft tissue (e.g., skin, tendons, ligaments, cartilage, muscle, vascular tissue, and/or other similar anatomic structures). Embodiments of the invention can enable advancing or retracting one or more suture strands (sequentially or simultaneously) through soft tissue at a single location or multiple strategically distributed locations. As such, the embodiments of the invention provide various superelastic suture passing devices capable of creating mattress suture attachments that increase the pullout force of the stitch. Embodiments of the invention also can enable contacting and penetrating soft tissue, for advancing or retracting suture strands, during less invasive access to anatomic regions where exposure to the soft tissue is compromised by the confined or difficult to reach space commonly associated with restricted access procedures.

The superelastic puncturing components of certain suture passing device embodiments of the invention can incorporate elongate superelastic members with sharpened distal ends, and contain eyelets or crochet hooks. The eyelets or crochet hooks can be formed in the superelastic elongate raw material by cutting at least one slot (axial or other relation to the superelastic members) in the raw material and thermally forming the slot(s) radially outward to form an opening large enough to pass at least one strand of suture. These suture passer embodiments can enable forming a mechanism to pass at least one strand of suture through soft tissue without having the suture strand bonded to a needle as a single integrated unit.

Certain superelastic suture passing device embodiments of the invention can provide a tubular housing with one or more lumens to compress and deploy one or more solid or hollow superelastic puncturing components that incorporate resilient preformed shapes and features to advance or retract one or more suture strands through soft tissue. Alternative suture passing device embodiments incorporate a modified grasper with one or more strategically placed deployment lumens to advance one or more superelastic puncturing components for positioning suture strands through soft tissue. Also described are superelastic suture passing device embodiments that position one or more snares through soft tissue for pulling one or more suture strands through the soft tissue.

Also, an embodiment of the invention includes a surgical device for passing suture through soft tissue. The surgical device can include at least one elongate superelastic member having a thickness and having a first resting configuration that defines at least one curve having a first radius of curvature greater than or equal to 3 times the thickness of the superelastic member. The surgical device also can include a thermally formed opening in the superelastic member, the opening adapted to receive at least one strand of suture. Moreover, the surgical device can include a superelastic member adapted to be straightened into a second configuration having a second radius of curvature larger than the first radius of curvature.

In another embodiment, a surgical device is disclosed for use in arthroscopic rotator cuff repair. This device contains at least one superelastic member having a first resting configuration that defines a first curve with a radius of curvature greater than or equal to 3 times a diameter of the superelastic member. The device also has a thermally formed opening in its superelastic member. The opening is adapted to pass at least one suture strand. Further, a sharpened tip on the device is adapted to puncture through a tendon. The device also includes at least one straightening mechanism adapted to compress the superelastic member into a second stressed configuration that defines a curve with a radius of curvature greater than 2 times a radius of curvature for the first resting configuration. There is an actuation mechanism associated with the superelastic member and the straightening mechanism. The actuation mechanism is adapted to advance and retract the superelastic member relative to the straightening mechanism.

The following is a detailed description of certain exemplary embodiments of the inventions. This detailed description is not to be taken in a limiting sense, but is made merely for the purpose of illustrating certain general principles of the inventions.

This patent application discloses a number of exemplary embodiments, mainly in the context of soft tissue repair and reinforcement accomplished through less invasive approaches (e.g. arthroscopic, laparoscopic, or other minimally invasive procedures). The superelastic suture passing embodiments disclosed herein can facilitate advancing or retracting one or more suture strands through any soft tissue to effectively attach the soft tissue to another anatomic structure (e.g. bone, muscle, tendon, etc.) or another region of soft tissue. The superelastic suture passing device embodiments of the invention can be used in such procedures as rotator cuff repair by enabling the creation of a mattress suture attachment knot between soft tissue (e.g. tendon) and bone, or meniscal repair by passing at least one suture strand through soft tissue at opposite sides of the tear. The superelastic suture passing device embodiments of the invention also enable positioning the small diameter straightening tubes with associated features (e.g. clamp mechanism) through a drilled bone tunnel then deploying the superelastic puncturing components on the other side to pass suture through avulsed boney attachment of ligaments (e.g. ACL).

Nevertheless, it should be appreciated that the superelastic suture passing devices can be applicable for use in other indications involving devices that are used to position one or more suture strands through soft tissue where access to the tissue is limited by a small opening into the cavity, confined space at the soft tissue interface, difficult to reach locations, or other anatomic limitation. The embodiments of the invention can be configured for the human anatomy; however, it should be noted that the embodiments of the invention can, in some cases, be tailored to other species, such as horses, by changing the geometry and sizes of the structures. In addition, the embodiments of the invention enable passing suture around soft tissue or other anatomic structures (e.g. around the neck of the gall bladder, vessels, or appendix to be tied prior to being cut and removed), especially if the superelastic puncturing components have blunt distal tips or are thermally formed into a flexible pigtail or other atraumatic end.

Certain exemplary embodiments of the invention can provide suture passing devices that incorporate superelastic puncturing components capable of penetrating, advancing, retracting, and/or snaring. The superelastic puncturing components of the suture passing devices can be fabricated from superelastic shape memory alloys. These superelastic puncturing components can elastically deform upon exposure to an external force (e.g. retracting into at least one straightening tube of the superelastic suture passing device) and return towards their preformed shape upon reduction or removal of the external force (e.g. advancing beyond the confines of the at least one straightening tube). The superelastic puncturing components can exhibit stress-induced martensite characteristics in that they transform from the preshaped austenite form to the more soft and ductile martensite form upon application of stress and transform back toward the more strong and hard austenite form once the stress is released or reduced; this can depend on the composition of the superelastic shape memory alloys which affects the temperature transition profile. Superelastic shape memory alloys also can enable straining the material numerous times without plastically deforming the material. Superelastic shape memory alloys are light in weight, and exhibit excellent tensile strengths such that they can be used as needles, snares, anchors, or other devices without dramatically increasing the weight or profile of the device. The utility of superelastic materials in puncturing components can be highlighted by the inherent properties of such materials; they can be able to withstand continuous and frequent deflections without plastically deforming or observing fatigue failures.

These superelastic puncturing components can also be elastically deflected into small radii of curvatures and return towards their preformed configuration once the external force causing the deflection is removed or reduced. Many other known metal, alloy, and thermoplastic materials can plastically deform, develop microcracks, or fracture when deflected into similar radii of curvature or exposed to comparable strains; as such these other metal, alloy, and thermoplastic materials do not return towards their original configuration when exposed to the amount of deflection such devices are expected to endure. Therefore superelastic puncturing components can inherently incorporate resilient flex regions, which conventional needles, snares, and/or anchors are unable to accommodate.

In addition, superelastic devices can permit deflections that result in larger strain than other metals, alloys, and polymers; this can enable compressing the superelastic puncturing components, other penetrating device, snare, and/or anchor into a low profile. As a result, superelastic puncturing components can be compressed into a low profile for advancing through less invasive access (e.g. smaller incisions) into the cavity and return towards their preformed shape thereby penetrating the target soft tissue(s) to enable advancing or retracting suture through the soft tissue. Similarly, superelastic snares can be deflected into a low profile for placement through soft tissue to enable retracting one or more suture strands through the soft tissue. In addition, superelastic anchors can be deflected into a low profile for positioning into bone and return towards their preformed shape once positioned.

Superelastic puncturing components can be fabricated from shape memory alloys (e.g. nickel titanium) demonstrating stress-induced martensite at ambient temperature. Of course, other shape memory alloys can be used and the superelastic material can alternatively exhibit austenite properties at ambient temperature. The composition of the shape memory alloy can be chosen to produce the finish and start martensite transformation temperatures (Mf and Ms) and the start and finish austenite transformation temperatures (As and Af) depending on the desired material response. When fabricating shape memory alloys that exhibit stress induced martensite the material composition can be chosen such that the maximum temperature that the material exhibits stress-induced martensite properties (Md) is greater than Af and the range of temperatures between Af and Md can cover the range of ambient temperatures to which the support members are exposed. When fabricating shape memory alloys that exhibit austenite properties and do not transform to martensite in response to stress, the material composition can be chosen such that both Af and Md are less than the range of temperatures to which the supports are exposed. Of course, Af and Md can be chosen at any temperatures provided the shape memory alloy exhibits superelastic properties throughout the temperature range to which they are exposed. Nickel titanium having an atomic ratio of 51.2% Ni and 48.8% Ti exhibits an Af of approximately −20° C.; nickel titanium having an atomic ratio of 50% Ni to 50% Ti exhibits an Af of approximately 100° C. [Melzer A, Pelton A. Superelastic Shape-Memory Technology of Nitinol in Medicine. Min Invas Ther & Allied Technol. 2000: 9(2) 59–60].

Such superelastic materials are able to withstand strain as high as 10% without plastically deforming. As such, these superelastic materials can be capable of elastically exerting a force upon deflection. Materials other than superelastic shape memory alloys can be used provided that they can be elastically deformed within the temperature, stress, and strain parameters required to maximize the elastic restoring force thereby enabling the superelastic device to exert a directional force in response to an induced deflection. Such materials can include other shape memory alloys, bulk metallic glasses, amorphous Beryllium, suitable ceramic compositions, spring stainless steel 17-7, Elgiloy™, superelastic polymers, etc.

Embodiments of the invention can provide superelastic suture passing devices for advancing or retracting suture through soft tissue during less invasive (e.g. arthroscopic, laparoscopic, or other minimal access) surgical procedures. In particular, the superelastic puncturing components of certain suture passing devices of the invention can contain or can be fabricated from superelastic wires, ribbon, bar, and/or tubing that can be deflected into a reduced profile and return towards their preformed shape after removal of the external force.

An additional benefit of superelastic suture passing devices can involve the ease of deployment and the rapid healing post-procedure. The small incision used to access the soft tissue and corresponding anchor structure during such procedures accelerates the healing process and reduces the visible scar. The superelastic puncturing components and snares of the suture passing device can be capable of being deployed through an arthroscopic, or laparoscopic approach, thereby potentially eliminating the need for long incisions to access the soft tissue and corresponding anchor structure.

The superelastic puncturing components and/or snares of the suture passing device can be fabricated in shapes designed to tailor the desired spring characteristics, radial stiffness, and axial stiffness to optimize the remote insertion of the superelastic puncturing components and/or snares through soft tissue. The ability to change parameters of various superelastic puncturing components and/or snares can be accomplished by the inherent properties of the annealed superelastic material. Alternatively, other components can be used to change the shape, exposed length, or other variable. The superelastic suture passing device can contain any number of superelastic puncturing components and/or snares integrated together, functioning independently, or operating collectively.

The suture passing device, and corresponding superelastic puncturing components and/or snares can be fabricated from at least one rod, wire, band, bar, tube, sheet, ribbon, other raw material having the desired pattern, cross-sectional profile, and dimensions, or a combination of cross-sections. The rod, wire, band, bar, sheet, tube, ribbon, or other raw material can be fabricated by extruding, press-forging, rotary forging, bar rolling, sheet rolling, cold drawing, cold rolling, using multiple cold-working and annealing steps, casting, or otherwise forming into the desired shape. The superelastic puncturing components or snares of the suture passing devices can be cut to the specified length, and into the desired pattern of eyelet slots, sharp needle tip, or other features, and are thermally formed into the desired 3-dimensional geometry. Conventional abrasive sawing, water jet cutting, laser cutting, EDM machining, photochemical etching, or other etching techniques can be employed to cut the superelastic suture passing devices, and corresponding superelastic puncturing components or snares from the raw material.

Ends or any sections of the rod, wire, band, sheet, tubing, ribbon, or other raw material can be attached by laser welding, adhesively bonding, soldering, spot welding, or other attachment means. Multiple rods, wires, bands, sheets, tubing, ribbons, other raw materials, or a combination of these can be bonded to produce a composite superelastic puncturing component, snare, or anchor. The superelastic puncturing component, and/or snare can alternatively be secured to another component of the suture passing device such as handle actuators, etc. using the processes listed above.

For several of the suture passing device embodiments below, the superelastic puncturing components and/or snares can be fabricated from at least one wire, tube, ribbon, sheet, rod, band or bar of nickel titanium material cut to the desired length and thermally formed into the desired 3-dimensional configuration. When thermally forming superelastic puncturing components, snares, anchors, or features in the puncturing components such as the eyelet opening or crochet hook, the superelastic materials, previously cut into the desired pattern and/or length, can be stressed into the desired resting configuration using mandrels and/or a forming fixture having the desired resting shape of the puncturing component, snare, or anchor, and the material is heated to between 300 and 600 degrees Celsius for a period of time, typically between 15 seconds and 10 minutes. Once the volume of superelastic material reaches the desired temperature, the superelastic material is quenched by inserting into chilled or room temperature water or other fluid, or allowed to return to ambient temperature. As such the superelastic puncturing components, snares, anchors, or specific features of the puncturing components (e.g. eyelet or crochet hook) can be fabricated into their resting configuration. When extremely small radii of curvature are desired, multiple thermal forming steps can be utilized to sequentially bend the rod, wire, band, sheet, tubing, ribbon or other raw material into smaller radii of curvature.

When fabricating the superelastic puncturing components from tubing, the raw material can have an oval, circular, rectangular, square, trapezoidal, or other cross-sectional geometry capable of being cut into the desired pattern. After cutting the desired pattern of sharpened tip and eyelets, the puncturing components can be formed into the desired shape, heated, for example, between 300° C. and 600° C., and allowed to cool in the preformed geometry to set the shape of the superelastic puncturing components.

When fabricating the superelastic puncturing components or snares from wires or other raw material type, the raw material can be configured with at least one diameter throughout the raw material. As such, the raw material can have a consistent diameter, a tapered diameter, or sections of varying diameter. The raw material is then cut into the desired pattern of sharpened tips and eyelets, and thermally formed into the desired 3-dimensional geometry. Opposite ends or intersections of thermally formed puncturing components and/or snares can be secured together or to other components of the suture passing device by using shrink tubing, applying adhesives, welding, soldering, mechanically engaging, utilizing another bonding means, or a combination of these bonding methods.

Once the superelastic puncturing components, snares, or anchors are fabricated and formed into the desired 3-dimensional geometry, they can be tumbled, sand blasted, bead blasted, chemically etched, ground, mechanically polished, electropolished, or otherwise treated to remove any edges and/or produce a smooth surface.

Holes, slots, notches, other cut-away areas, or regions of ground material can be incorporated in the superelastic puncturing component, snare, or anchor design to tailor the stiffness profile. Cutting and treating processes described above can be used to fabricate the slots, holes, notches, cut-away regions, and/or ground regions in the desired pattern to taper the stiffness along the superelastic puncturing component, snare, or anchor, focus the stiffness along the length of, reinforce specific regions of, or otherwise customize the stiffness profile of the puncturing component, snare, or anchor.

FIGS. 1a to d show side views of the steps involved in fabricating a superelastic puncturing component 10 from superelastic raw material. The superelastic puncturing component can be fabricated from wire, ribbon, rod, band, bar, or other cross-sectional geometry having a diameter between 0.010" and 0.200".

Figure 1C:
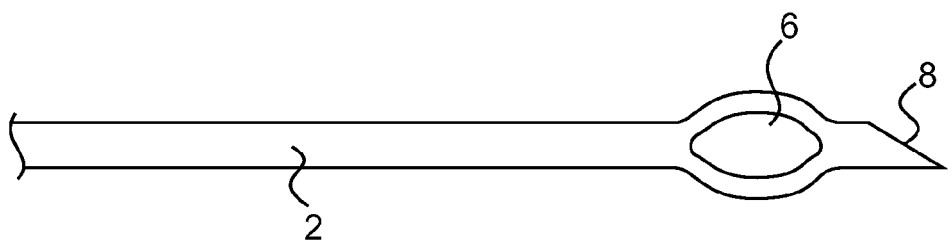
Figure 1D:
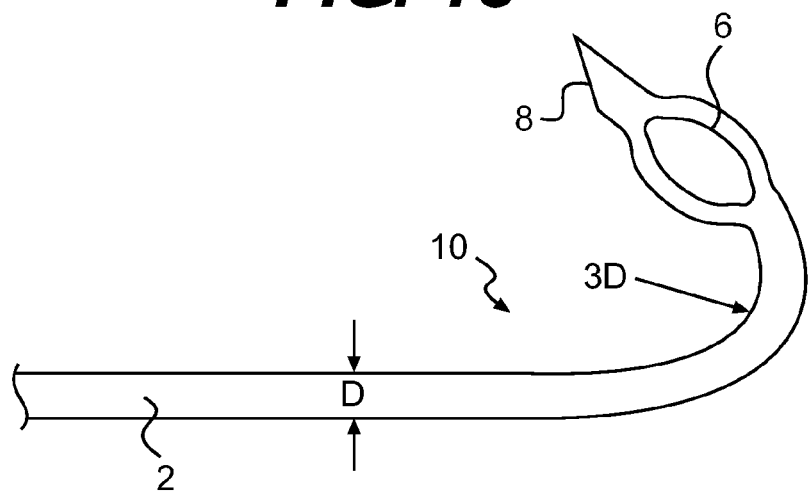

The superelastic wire 2 (or other geometry raw material) is cut, with methods described previously, to define an eyelet (or keyhole) slot 4 and a sharpened tip 8. In this case a beveled tip is illustrated; it should be noted that alternative sharpened tips (e.g. cutting edge, pointed, etc.) can be fabricated. In the embodiment shown in FIG. 1b, the eyelet (or keyhole) slot 4 is created just proximal to the sharpened tip 8 so the eyelet (or keyhole) can be advanced through the tendon once the superelastic puncturing component is allowed to return towards its preformed, resting shape, after being deflected (compressed) into a low profile for deployment. As shown in FIG. 1c, the eyelet slot 4 is expanded in opening diameter (e.g. with a mandrel or forming fixture) and thermally formed in this configuration to form the eyelet (or keyhole) 6. Nickel titanium wire having a diameter of 0.040" has been used to fabricate superelastic puncturing devices with the manufacturing steps described above and below. An axial slot having a length of 0.120" was cut in the nickel titanium raw material and was thermally formed with a mandrel into an opening having an internal width of 0.040"; this opening was demonstrated to be adequate of passing the suture strand sizes used in rotator cuff repair or meniscal repair. Larger slots can be created but significantly increasing the slot length adversely impacts the column strength of the superelastic puncturing component and decreases the stiffness of the thermally formed curve, since the keyhole in the illustrated embodiments resides just distal to the curve as shown in FIG. 1d. Smaller slots can also be created, especially when smaller openings are suitable, but the stresses exerted on the raw material at the ends of the slots, while thermal forming the opening, increases as the slot length decreases.

As shown in FIG. 1d, the superelastic puncturing component 10 is then thermally formed into the desired 3-dimensional geometry having at least one curve with a radius of curvature greater than or equal to 3 times the diameter of the superelastic puncturing component. As the radius of curvature for a particular superelastic puncturing component curve increases, the stress, observed when compressing the curve into a more straight, low profile configuration, decreases. The thermally formed 3-dimensional puncturing component resting configuration is capable of matching the shape and stiffness profile of the puncturing component to the required access path capable of puncturing the soft tissue (e.g. tendon) and passing suture. The superelastic puncturing component 10 in FIG. 1d is shown with a single curve having a radius of curvature equal to 3 times the thickness; it should be noted that the superelastic puncturing component (as well as the snares described below) can be thermally formed into multiple curves having multiple radii of curvature that tailor the reach and pattern of the superelastic puncturing component to the access region in the body cavity.

The superelastic puncturing components have at least one diameter for wires, at least one width and at least one height for bars and bands, and at least one length configured to produce the desired stiffness and force profile. The diameter or other parameter can vary throughout the superelastic puncturing components to vary the stiffness profile and resulting response. The length of the superelastic puncturing components can also be tailored to address varying access requirements.

Figure 2A:
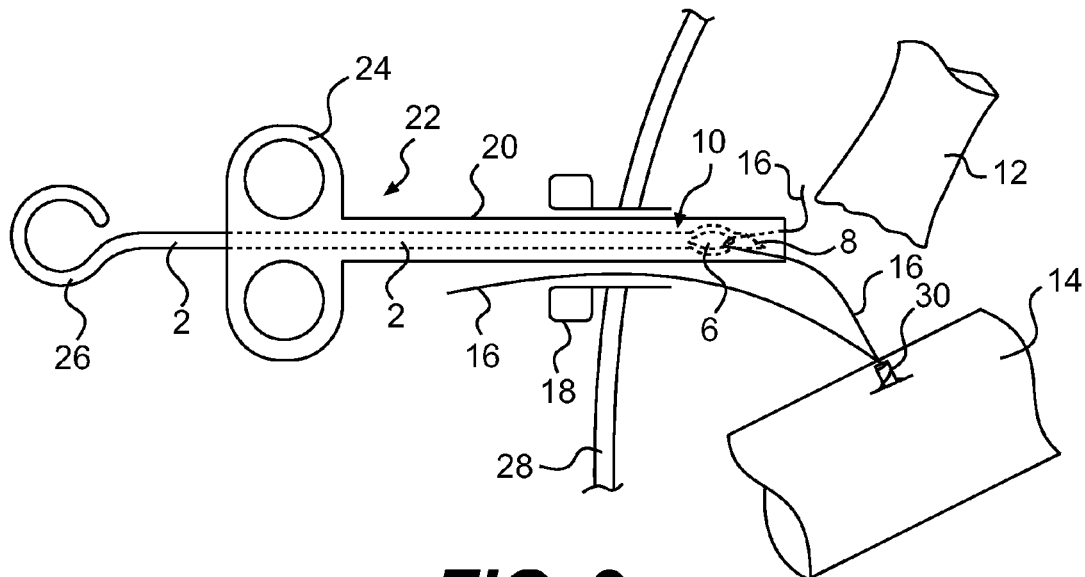
FIGS. 2a to c show the steps involved in using a superelastic suture passing device to secure a soft tissue (e.g. tendon) region to another anatomic structure (e.g. bone) during arthroscopic or laparoscopic procedures.
Figure 2B:
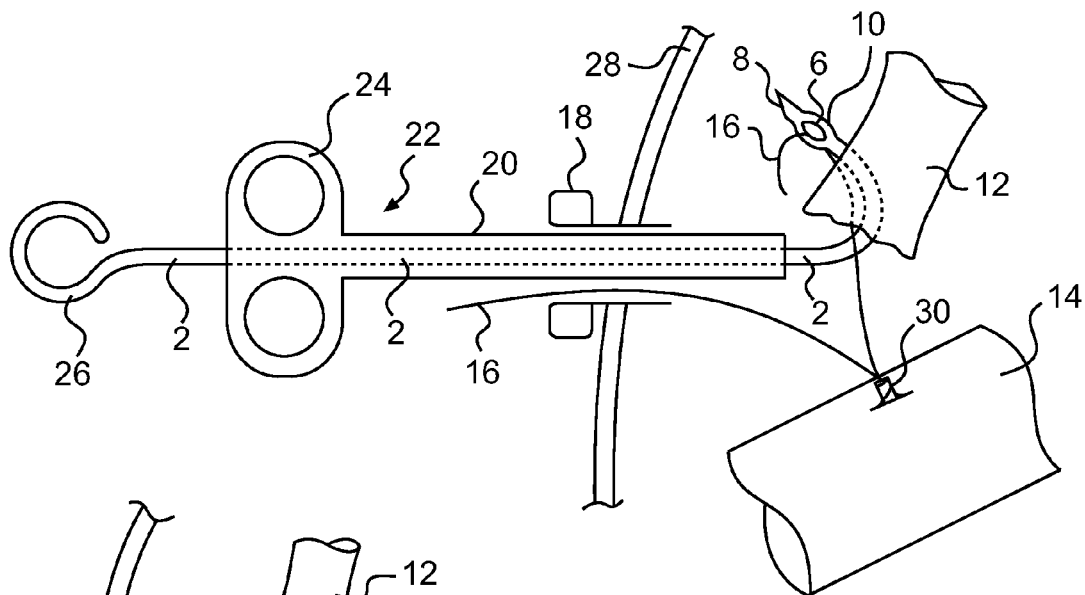
Figure 2C:
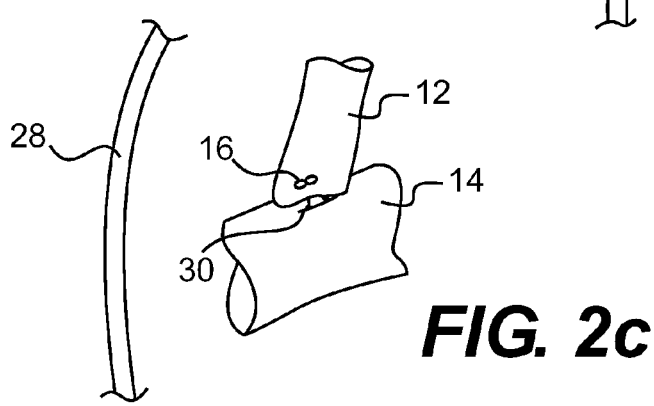

FIGS. 2a to c show the steps used to repair soft tissue, or reattach soft tissue (e.g. tendon) to another anatomic structure (e.g. bone) during minimally invasive access (e.g. arthroscopic, laparoscopic, or other approach) into the body cavity. A conventional cannulae, trocar or other portal is used to access the cavity through the skin 28 and underlying tissues.

The superelastic suture passing device 1 contains a straightening tube 20 attached to a handle 24, and a superelastic puncturing component 10 integrating an actuator knob at the proximal end and defining a sharpened tip 8 and eyelet (or keyhole) 6 at its distal end. The straightening tube 20 maintains the superelastic puncturing component 10 in a low profile for insertion through the port or trocar 18 and into the cavity, as shown in FIG. 2a. One suture strand 16 can be fed through the eyelet 6 prior to compressing the superelastic puncturing component 10 for deployment and advancing the suture passing device into the cavity. Alternatively, the superelastic puncturing component can be partially compressed when the at least one strand is positioned through the eyelet 6.

As shown in FIG. 2b, the superelastic puncturing component 10 is advanced through manipulation of the actuator knob 26 beyond the distal end of the straightening tube 20. Once the superelastic puncturing component extends beyond the confines of the straightening tube 20, the superelastic puncturing component 10 returns towards its preformed, resting configuration defining a curve capable of positioning the sharpened tip 8 and subsequently the eyelet 6 containing the suture strand 16 through the soft tissue 12. Once the eyelet 6 of the superelastic puncturing component 10 has penetrated through the soft tissue 12, the suture strand 16 is grasped and withdrawn from within the eyelet 6 ensuring that the suture strand 16 is not removed from the soft tissue.

The other suture strand 16 can then be fed through another region of the soft tissue 12 with a similar approach to produce a mattress suture knot (as described below) and provide better engagement of the soft tissue (e.g. tendon) to other anatomic structure (e.g. bone) 14. Once all desired passes of suture through the soft tissue have been completed, the suture(s) can be tied, as shown in FIG. 2c. This attaches the soft tissue (e.g. tendon) to other anatomic structure (e.g. bone). It should be noted that a bone anchor can be used to secure one or more suture strands to the anchoring anatomic structure (e.g. bone) 14 prior to introducing the corresponding suture strands through the soft tissue. Any number of stitches and any configuration of suturing (e.g. mattress) can be created with the superelastic suture passing device of the invention.

The approach described above details advancing suture strands through soft tissue (e.g. tendon, muscle, or other tissue). It should be noted that one or more suture strands 16 can alternatively be fed through the eyelet 6 after penetrating the soft tissue with the superelastic puncturing component 10, not shown. Then, the suture strand can be retracted through soft tissue, as opposed to advancing which is described above. When retracting suture through soft tissue, the eyelet opening needs to be enlarged since the suture strand would need to be advanced remotely and a larger opening facilitates proper placement of the suture into the eyelet. Alternatively, a crochet hook can replace the eyelet so the superelastic puncturing component can be used to hook onto the suture and pull the suture through the soft tissue.

The approach described above utilizes a superelastic suture passing device with superelastic puncturing components to pass the suture through soft tissue in confined or difficult to reach spaces. An alternative approach, not shown in the Figures, is to incorporate a steering mechanism to the puncturing component, and/or snare (formed from superelastic materials or other metal or alloy components). By slotting the proximal region of the puncturing component towards the sharpened tip, with processes described previously, two pull-wires can be formed which are independently actuated by a proximal handle, not shown, to manually deflect the puncturing component into a curve; the curve angle and radius is defined by the distance from the sharpened tip at which the pull-wires separate and the stiffness of the puncturing component assembly. A guide-coil or other radially restraining component can be housed around the pull-wires to specify the stiffness of the puncturing component assembly and further define the radius of curvature and angle of deflection of the distal region of the superelastic puncturing component as the pull-wires are actuated. Snares can also be fabricated as steerable by forming the snare with features described for the puncturing components. In addition, the suture passing device straightening tubes described below can alternatively be made steerable by fabricating the straightening tubes with one or more pull-wires secured to the straightening tube at predetermined locations, which, when actuated, are able to deflect the straightening tube into a curve.

Rotator cuff repair is one example of arthroscopic soft tissue repair that the superelastic suture passing devices of the invention enable reliable and accurate suturing of a soft tissue region to other anatomic structure. A posterior or lateral portal is routinely used to visualize the rotator cuff tear arthroscopically and access the joint through a lateral or anterolateral portal. The bony surface is prepared to stimulate healing of the rotator cuff. The rotator cuff is also prepared to create a fresh edge. Through this lateral working portal, a standard or superelastic suture anchor is placed into the bone and is secured in place. The sutures can be pulled out of the cannulae used to access the soft tissue and one of these suture strands is threaded through the eyelet in the superelastic puncturing component of the superelastic suture passing device. The superelastic puncturing component is then retracted inside the more rigid straightening tube such that it compresses into a low profile. The straightening tube of the superelastic suture passing device is then inserted into the arthroscopic cannulae. At this point the superelastic puncturing component is advanced out of the tip of the straightening tube and through the undersurface of the rotator cuff and the suture is thus advanced from the bone side to the opposite side of the cuff tissue. At this point another portal can be used for a conventional grasper to retrieve the suture on the superior surface of the rotator cuff tissue. The superelastic suture passing device is withdrawn and the other suture strand can be passed in similar fashion to the first. Alternatively, multiple suture strands can be passed simultaneously with the aid of a double barrel device, described below. This allows a mattress type suture to be tied with ease on the superior aspect of the cuff.

Existing rotator cuff repair applications performed all arthroscopically tend to create just a simple suture knot with only one suture pass through the soft tissue. Passing a mattress suture with conventional approaches is exceedingly difficult and cumbersome because conventional suture techniques require rotation of the needle through soft tissue in the confined cavity. Also, rigid conventional needles can be difficult to maneuver in confined regions, have larger diameters, have fixed curves, and can be more difficult to pass through cannulaes. As such, the existing techniques can be mechanically inferior and have a higher rate of pullout than a mattress suture configuration created with the superelastic suture passing device of the invention.

Figure 9C:
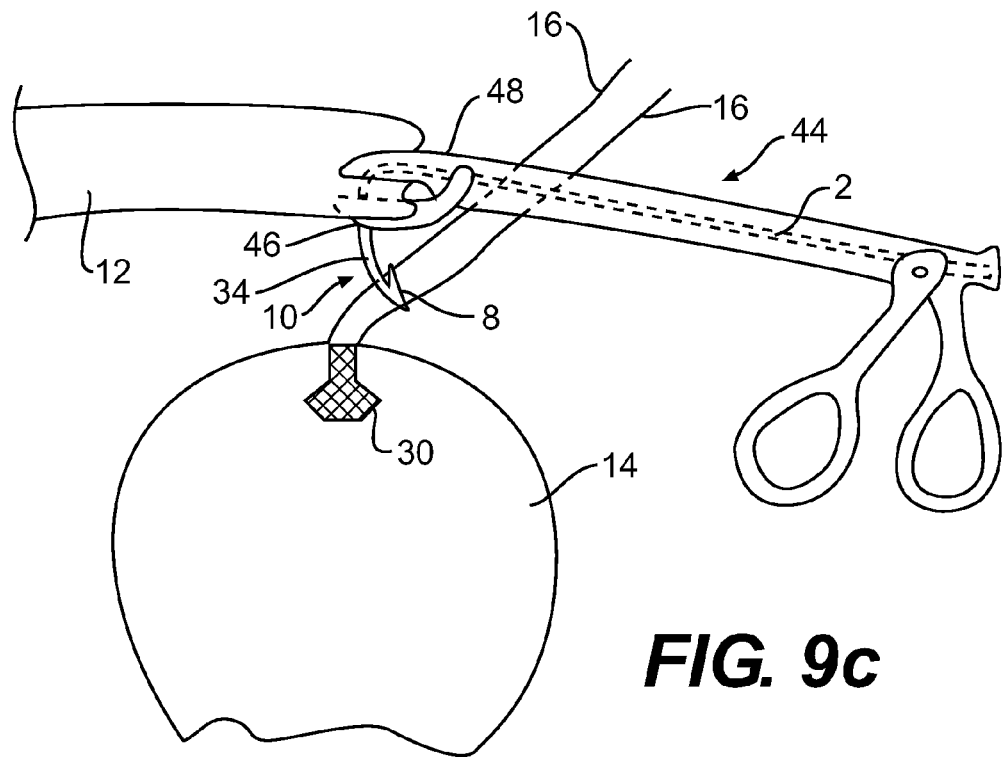
FIGS. 9c and d show perspective views of another grasping, suture passing device embodiment that incorporates a superelastic puncturing component with a crochet hook to engage and pull at least one suture strand through soft tissue.
Figure 9D:
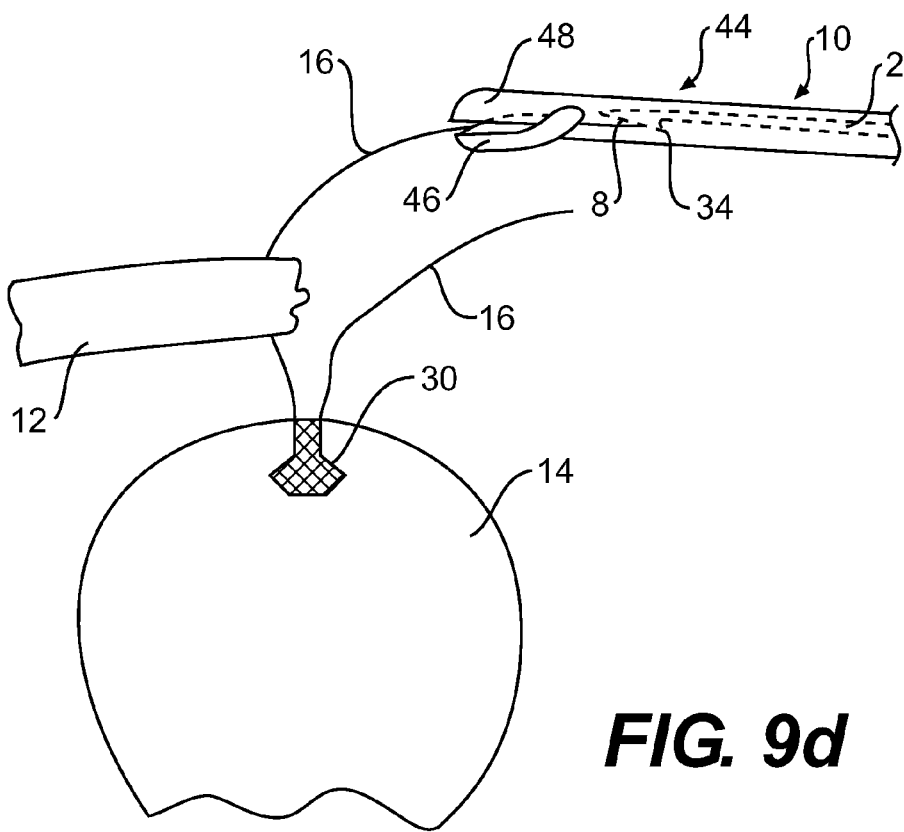
FIG. 9a shows a perspective view of a grasping, suture passing device embodiment that incorporates a superelastic puncturing component advancing and retracting through a dedicated lumen.
FIG. 9b shows a perspective view of an alternative grasping, suture passing device embodiment that incorporates a double barrel straightening tube mechanism for manipulating two or more superelastic puncturing components through separate tracts.

An alternate method for rotator cuff repair using the superelastic suture passing device of the invention is to use the same basic scenario described above and insert the superelastic puncturing component through the more rigid straightening tube of the superelastic suture passing device into the joint on the superior aspect of the rotator cuff. The superelastic puncturing component is then advanced from the superior aspect of the cuff down through the soft tissue towards the bony side and a crochet hook is used to retrieve the suture attached to the suture anchor on the bottom side of the cuff, as shown in FIG. 9c. The suture is then pulled back through the cuff to the rotator cuff side, as shown in FIG. 9d. The same basic principles and steps apply for retrieving the other limb of the sutures and the mattress suture is tied down.

A similar approach can be used to pass suture through the labrum as with a Bankart lesion for an unstable shoulder, to pass suture through discrete points along the meniscus for repairing a meniscal tear, to pass suture through any other soft tissue that has a tear that must be closed, or to pass suture through any other soft tissue that needs to be attached to bone or other anatomic structure. The embodiments of the invention can be modified to incorporate a blunt or atraumatic (e.g. pigtail) distal end on the superelastic puncturing components to enable passing suture around (as opposed to through as described for the embodiments below) anatomic structures such as the gall bladder, vessels to be ligated, the appendix for subsequent removal, or other organ or tissue. These atraumatic suture passing devices (not shown) can also be used to pass one or more suture strands multiple times around the anatomic structure to increase the reliability and strength of the knot, once tied.

The embodiments of the invention described in this specification can also be used for closing dissections in organs or vessels; creating a purse-string around the bowel, sphincter, trachea, or other tubular anatomy for reinforcement or diameter reduction; reducing the effective volume of, or completely isolating an atrial appendage for removing stasis regions commonly associated with embolic complications for atrial fibrillation patients; or other soft tissue repair procedure that involves passing one or more suture strands within a confined or difficult to reach space.

FIGS. 3a to d show side views of four potential superelastic puncturing component configurations. Each superelastic puncturing component incorporates an eyelet (or keyhole) 6 and sharpened tip 8 as described in the embodiment in FIG. 1d. The superelastic puncturing components in FIGS. 3c and d have smaller radii of curvature than those in FIGS. 3a and b. The embodiment in FIG. 3b has a smaller angle of curvature than that in FIGS. 3a, 3c, and 3d. All of these configurations can direct the passing of suture through soft tissue but can provide different pathways for the suture strand to pass through soft tissue thereby accommodating different access sites to the soft tissue and/or different soft tissue locations.

FIGS. 4a to d show a superelastic puncturing component that can function as a penetrating snare embodiment. This snare embodiment can be used to pull suture through soft tissue instead of advancing. A longer eyelet slot 4 can be created in the distal section of raw wire material 2 and a larger eyelet (or keyhole) 6 can be formed. Stressing a wire containing a relatively long slot into a curve can cause the inner section of wire to deflect inward as the outer section of wire defines the curve. This can produce a larger eyelet 6 without having to thermally form the eyelet with a mandrel independently from forming the desired shape of the superelastic needle. As shown in FIGS. 4b to d the cross-section of the raw wire material 2 can be circular, elliptical, or other geometry.

Figure 16A:
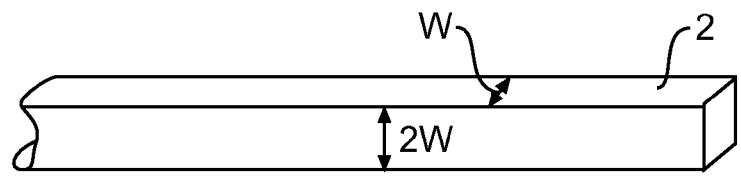
FIGS. 16a to k show representative steps for fabricating an integrated, dual distal section superelastic puncturing component embodiment formed from a single superelastic raw material.
Figure 16B:
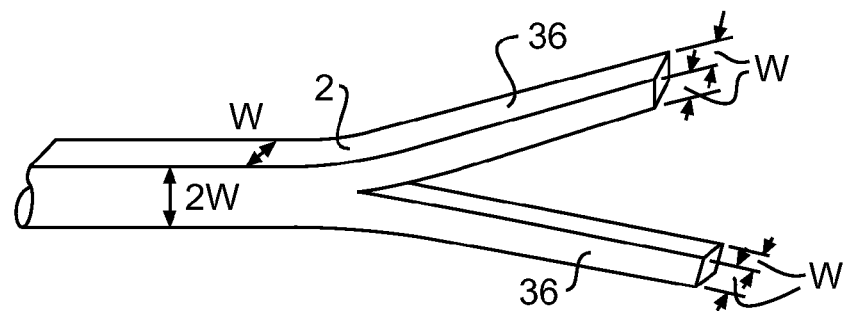
Figure 16C:
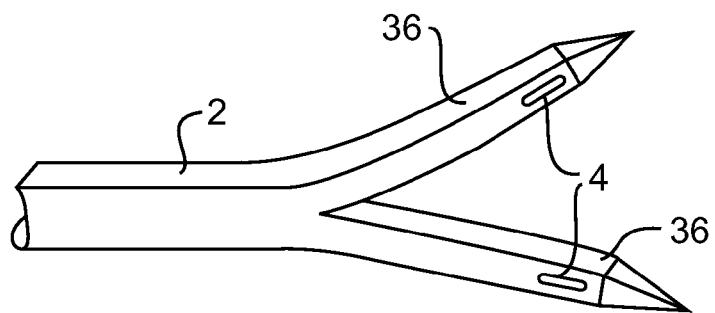
Figure 16D:
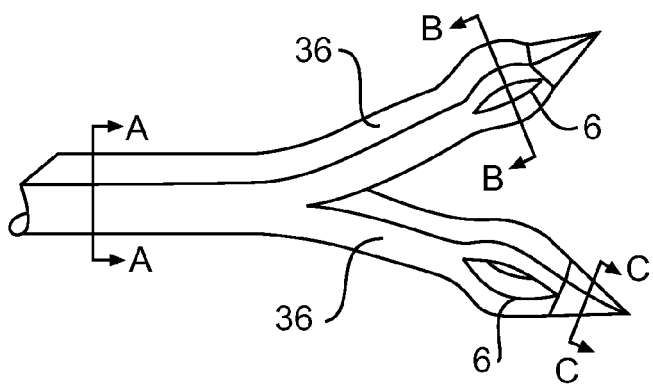
Figure 16E:
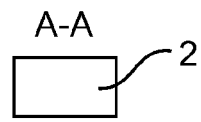
Figure 16F:
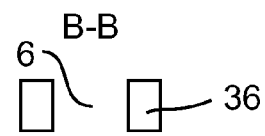
Figure 16G:
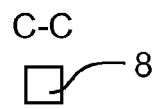
Figure 16H:
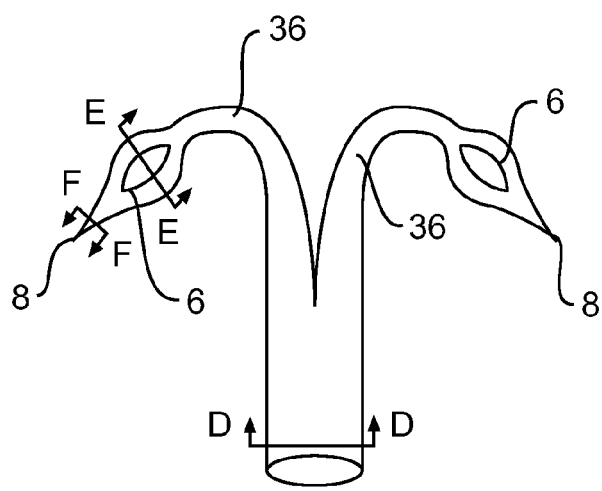
Figure 16I:
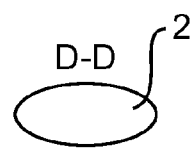
Figure 16J:
Figure 16K:
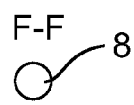

FIGS. 5a to d show a side view and three cross-sectional views of a superelastic puncturing component that incorporates two integrated penetrating sections. The raw material 2, shown in FIG. 16a (e.g. wire, bar, or ribbon raw material), is slotted from the distal end for a predetermined length, as shown in FIG. 16b. Each puncturing component section 36 is then cut to form an eyelet 6 and sharpened tip 8, as shown in FIG. 16c. The eyelet (or keyhole) 4 slots can be thermally formed to produce an opening 6 capable of passing at least one suture, as shown in FIGS. 16d to g. If bar or ribbon raw material is used, the puncturing component can be chemically etched, sand or bead blasted, and electropolished to break the edges and form more tubular ends to the integrated puncturing component. This post-processing can also be used for wire raw material but is most useful when using ribbon or bar raw material. If the initial raw material is a bar or ribbon having a rectangular cross-section with one side having a width W and the other having a length 2×W, then enough post-processing removal of material will produce two sides of the integrated puncturing component having a curved (somewhat circular) cross-section, as shown in FIGS. 16h to k. This superelastic puncturing component embodiment enables simultaneously penetrating two discrete soft tissue locations and advancing, or retracting, two separate suture strands through the soft tissue. The puncturing component sections 36 can be thermally formed into their desired curve (the same curve or differing angles and/or radii of curvature) and separation to define the relative locations of the suture strands along the soft tissue. It should be noted that more than two integrated but discrete superelastic puncturing components can be fabricated by creating more than one slot extending from the distal end of the raw material. In addition, the integrated but discrete superelastic puncturing components can be preformed to curve in the same direction but at spaced distances (axially, radially, or other direction relative to the elongate superelastic member). Alternatively the discrete segments of the integrated superelastic puncturing components can extend away from each other such that they curve opposite (e.g. 180 degree), orthogonal, 45 degrees, or at any angle relative to each other.

FIG. 6 shows a superelastic puncturing component 10 that incorporates a crochet hook 34. The crochet hook 34 can be fabricated by cutting a slot from one side of the wire raw material 2 and extending the slot into the wire at an angle relative to the axis of the wire raw material. Then the crochet hook 34 can be preshaped by placing a temporary shim in the slot and thermally forming the hook in this outward orientation. The sharpened tip 8 is then cut in the raw material just distal to the distal end of the slot that defines the crochet hook 34. It should be noted that the crochet hook slot can alternatively be cut in a shepherd hook or other configuration.

FIGS. 7a to c show the steps in forming a superelastic puncturing component 10 from tube raw material. A tube 38 of superelastic material is cut to define a bevel (or other sharpened tip configuration) 8 and an eyelet (or keyhole) 6. In this case, the eyelet (or keyhole) does not need to be enlarged during thermal forming, although thermally forming in an expanded orientation is an option. As FIG. 7c shows, the cut tube is then thermally formed into the desired puncturing component configuration.

Figure 8B:
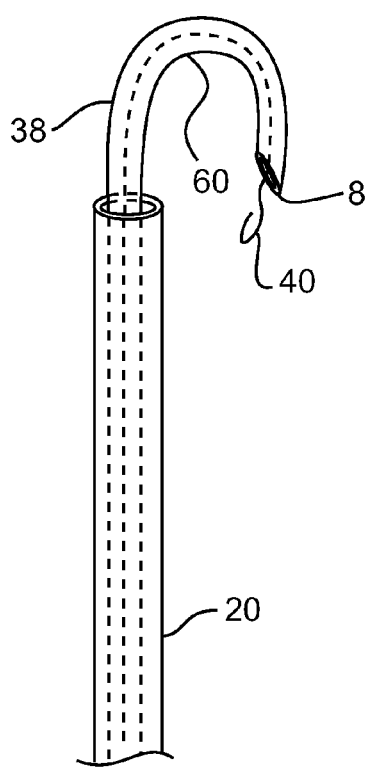
FIGS. 8b to d show side views of three relative positions in which the superelastic puncturing component embodiment in FIG. 8a is retracted inside a straightening tube of the suture passing device.
Figure 8C:
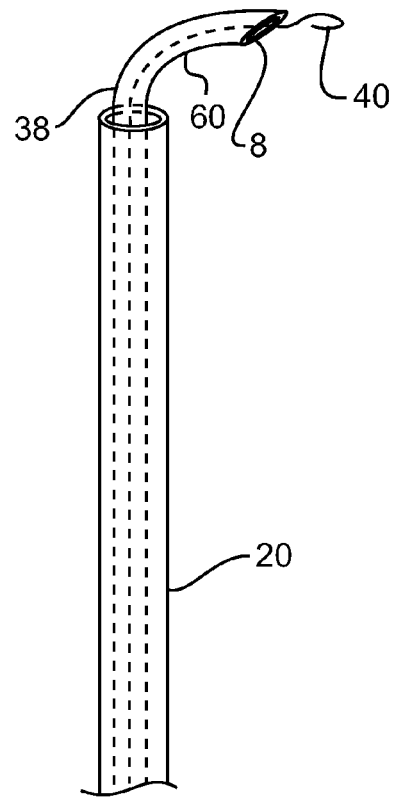
Figure 8D:
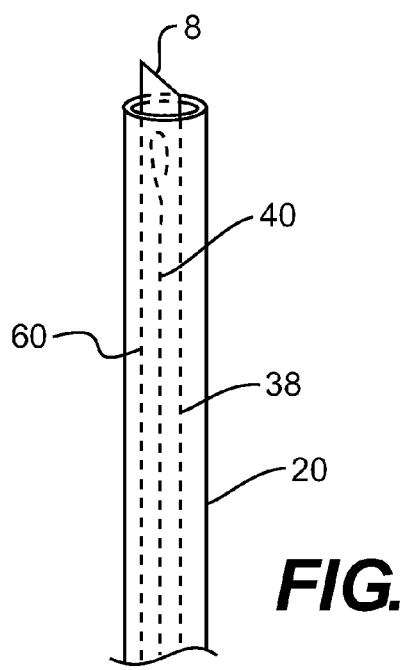

FIG. 8a shows a superelastic snare 60 used to position a snare wire 40 through soft tissue for pulling a suture strand through the soft tissue. The superelastic snare 60 incorporates tube raw material 38 formed into the preformed geometry and cut to define a sharpened tip 8. The snare wire 40 can also be fabricated from superelastic raw material and thermally formed into the desired shape. The snare wire 40 in FIG. 8a incorporates a shepherd's hook to facilitate engaging suture and pulling suture through the sharpened tube. As shown in FIGS. 8b to d, a straightening tube 20 can be incorporated in this superelastic suture passing device design to change the curve geometry of the superelastic snare and enable utilizing a single snare configuration for multiple applications with different access requirements. As the straightening tube 20 is advanced over the superelastic snare 60, the distal curve becomes less pronounced. As the straightening tube 20 is further advanced, the superelastic snare 60 compresses into a low profile for deployment through a cannulae, trocar, or other portal, as previously described. The straightening tube 20 in this embodiment and previous embodiments can also be thermally formed into a desired curve.

FIG. 9a shows a superelastic grasping, suture passing device 44 capable of capturing soft tissue and advancing or retracting strands (limbs) of suture through the captured soft tissue. The grasping, suture passing device 44 incorporates an upper jaw 46, which moves relative to a lower jaw 48. A stylet actuator 56 rotates the upper jaw 46 relative to a pivot connector to the lower jaw 48, and is manipulated by a proximal handle 45. The grasping, suture passing device 44 captures tissue prior to deploying the superelastic puncturing component and advancing the suture through the soft tissue. This grasping, suture passing device 44 can incorporate a lumen through the length; the lumen communicates with a proximal opening, not shown, and a distal opening, shown in FIG. 9a. The superelastic puncturing component 10 is contained within the lumen 52 of the grasping, suture passing device 44. The superelastic puncturing component is retracted into the lumen to compress the puncturing component into a low profile for deployment or in preparation for insertion through the captured soft tissue. Once soft tissue is captured between the upper and low jaws, the superelastic puncturing component is advanced through the soft tissue. An opening 50 in the upper jaw 46 directs the superelastic puncturing component's path through the soft tissue. This opening can be created such that a thin edge extends partially or completely around the upper jaw profile. In the preferred configuration, the opening extends through the middle region of the upper jaw and completely through the distal tip of the upper jaw such that the upper jaw can be removed from around the side of a suture strand once the suture is passed and the soft tissue is released. Once the superelastic puncturing component is positioned through the soft tissue, the suture is removed from the eyelet, the superelastic puncturing component is retracted inside the lumen, and the soft tissue is released from the jaws of the grasping, suture passing device 44.

The grasping, suture passing device 44 in FIG. 9b incorporates two straightening tubes 54 attached to a clamp. The clamp contains an upper jaw 46 and a lower jaw 48. The upper jaw rotates about a pivot relative to the lower jaw and enables capturing soft tissue between the jaws. Alternatively, not shown, both jaws can be moveable relative to each other or another fixed location. Once soft tissue is captured, two superelastic puncturing components can be penetrated through the soft tissue and can be used to advance (or retract) suture through the soft tissue. The upper jaw (and/or lower jaw if made moveable) of the clamp in this and other grasping, suture passing device embodiments, can also be used to engage the suture strand(s) once the suture is advanced through the soft tissue to further enable grasping the suture once positioned for retracting the suture into a position that the knots can be tied with the suture strands pulled outside the cannulae.

Figure 11B:
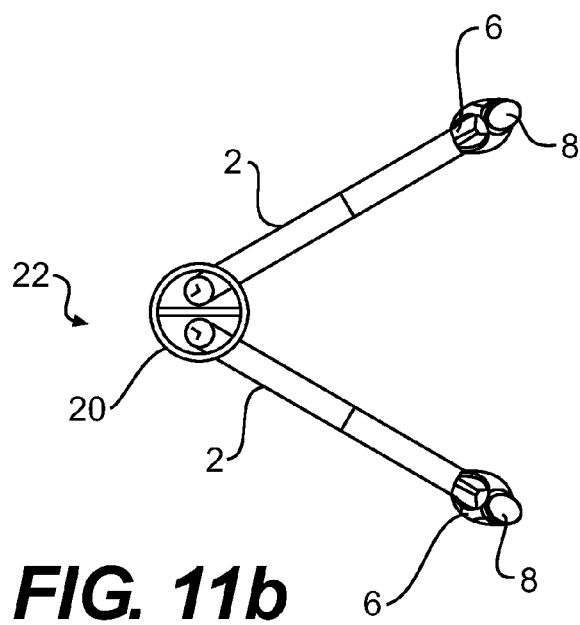
FIGS. 11a, b, and c show a side view, an end view, and a top view of the double barrel, suture passing device of FIGS. 10a to c in the deployed, resting configuration.
Figure 11A:
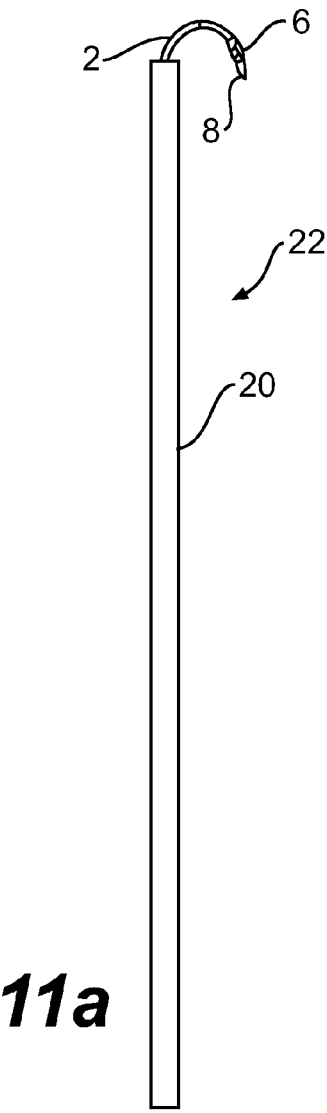
Figure 11C:
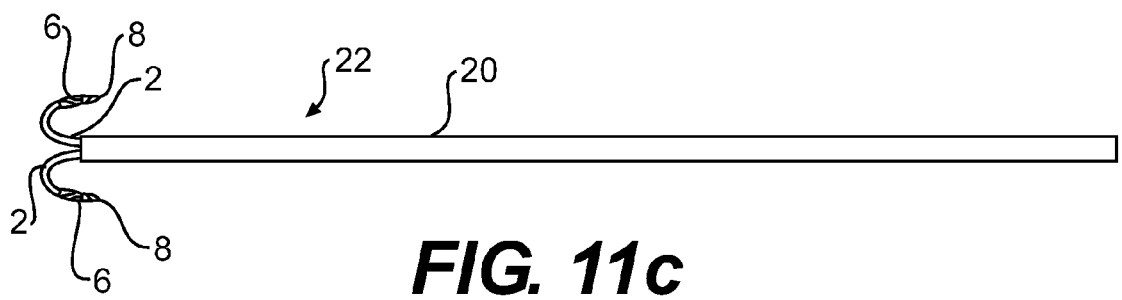

The straightening tubes can be separated by a distance, $D_{sep}$, designed to ensure the sites where the puncturing components penetrate soft tissue, thus the strands of suture, can be separated by at least 3 mm and preferably greater than or equal to 5 mm to optimize the bond strength once the knot of the suture is tied without tearing the soft tissue with the suture. One way to ensure adequate suture strand separation is to separate the straightening tubes by at least 3 mm and preferably 5 mm, as shown in FIG. 9b. In this case, the superelastic puncturing components can advance outside the straightening tubes such that they extend parallel or at an outward angle to ensure the specified spacing. Alternatively, the straightening tubes can be closely approximated, as shown in FIGS. 10a to c, and the superelastic puncturing components can be angled outward relative to each other (as shown in FIGS. 11a to c) such that when they are advanced through soft tissue the puncture sites can be separated by at least 3 mm and preferably greater than 5 mm. For example, a 60 degree angular separation between adjacent superelastic puncturing components, with a suture passing device having a diameter of approximately 4 mm and a distance from the compressed puncturing component to the clamped soft tissue of 3 mm, produces a spacing of approximately 3 mm. A 90 degree angular separation between adjacent superelastic puncturing components, with a suture passing device having a diameter of approximately 4 mm and a distance from the compressed puncturing component to the clamped soft tissue of 2.5 mm, produces a spacing of approximately 5 mm. As such, the larger the angle the superelastic puncturing components extend outward relative to each other, the shorter the distance from the compressed superelastic puncturing component to the clamped tissue and/or the larger the separation from the suture strand placement through soft tissue. Alternatively, the ends of the straightening tubes or discrete sections of the straightening tube can be axially offset relative to each other to create the desired spacing along the clamped soft tissue as the superelastic puncturing components extend beyond the straightening tubes and curve towards thus penetrating soft tissue.

It should be noted that a single straightening tube segmented into two or more sections (e.g. multi-lumen tubing) can be used in lieu of separate straightening tubes 54, as shown in FIGS. 10a to c. Alternatively, a single straightening tube having a lumen profile and cross-sectional area capable of housing multiple superelastic puncturing components.

In addition, the straightening tubes can incorporate curved distal ends having a larger radius of curvature and/or a smaller angle of curvature than that for the superelastic puncturing components. Incorporating curved ends on the straightening tubes for this or other embodiments, facilitates compressing the superelastic puncturing components by gradually straightening as opposed to abruptly deflecting the superelastic puncturing components. In addition, curved straightening tubes produce a more circular path as the sharpened tip of the superelastic puncturing device advances from the straightening tubes; this path better mimics the motion of rotating a needle through soft tissue, which is a common approach with conventional suturing techniques using rigid needles with attached suture strands.

The other basic application for arthroscopic rotator cuff repair, as described above, involves the use of an articulated grasping, suture passing device 44 that is cannulated to allow passage of the superelastic puncturing component, as previously described, and shown in FIGS. 9c and d. The grasping, suture passing device 44 clamps tissue to allow the operator to manipulate the position of the rotator cuff or other soft tissue to the desired location before passing the superelastic puncturing component and separate suture strand(s). An arthroscopic grasping, suture passing device 44, as shown in FIGS. 9c and d, is a long instrument with a handle that allows one to open and close the jaws for temporarily clamping tissue. The grasping, suture passing device 44 can be made cannulated by incorporating at least one straightening tube (as shown in FIG. 9b) secured to the device, or inherently defining at least one lumen that extends from the shaft of the device through the upper and/or lower arms, or between the arms of the grasping, suture passing device (as described above and shown in FIGS. 9a, 12a to c) to allow passage of suture and the superelastic puncturing component.

The scenario for usage of these grasping, suture passing device embodiments for arthroscopic rotator cuff (or other soft tissue) repair is described below and shown in FIGS. 9c and d, FIGS. 12a to c, and FIGS. 13a to d. A lateral portal can be used to prepare the bone as described previously and a suture anchor 30 is placed. The suture strands can be brought outside the cannulae and the superelastic puncturing component is advanced out of the lumen 52 of the grasping device 44 enough to insert one strand (limb) of the suture through the eyelet 6 of the superelastic puncturing component 10. The superelastic puncturing component is then retracted back into the lumen 52 of the grasping, suture passing device 44 such that the superelastic puncturing component is compressed into a low profile.

Figure 12C:
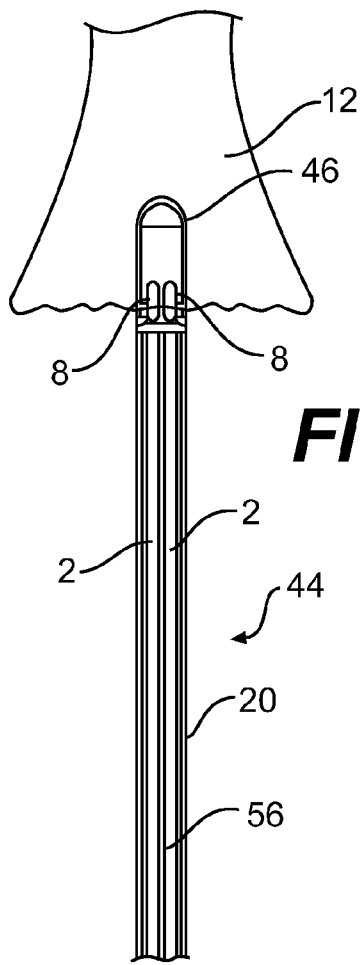
FIGS. 12a, b, and c show a side view, an end view, and a top view of a double barrel, grasping, suture passing device in the compressed, low profile configuration.
Figure 12A:
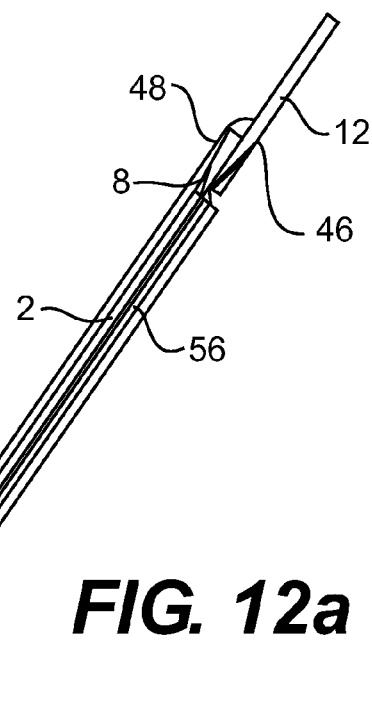
Figure 12B:
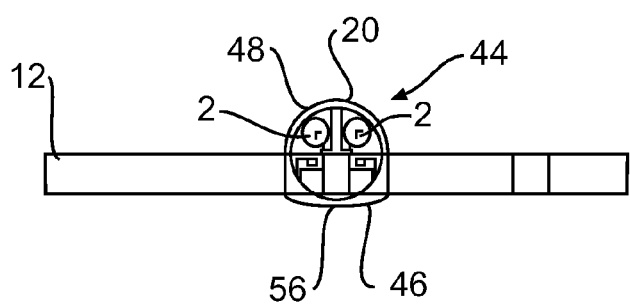
Figure 13A:
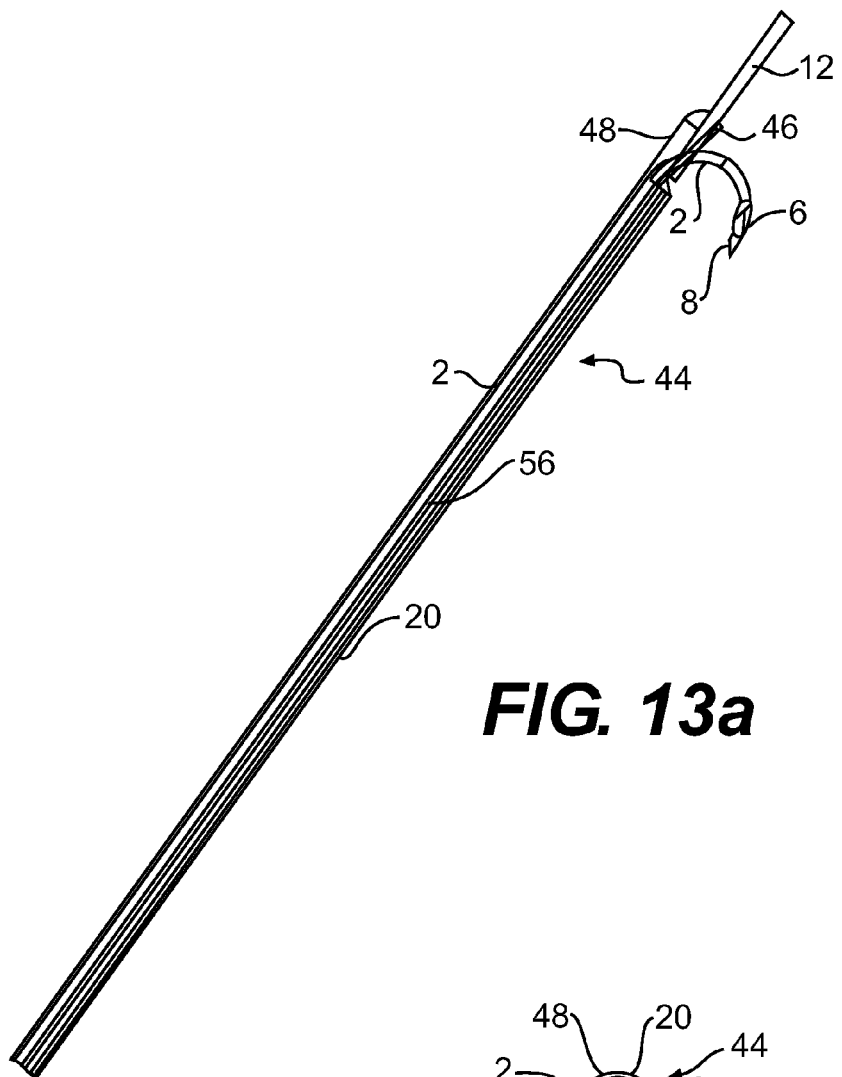
FIGS. 13a, b, c, and d show a side view, an end view, a top view, and a perspective view of the double barrel, grasping, suture passing device in FIGS. 12a to c in the deployed, resting configuration.
Figure 13B:
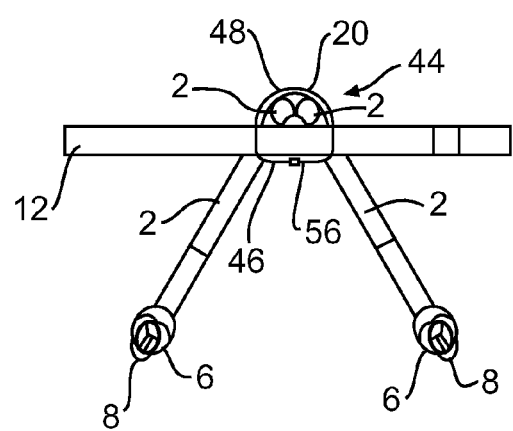
Figures 13C, 13D:
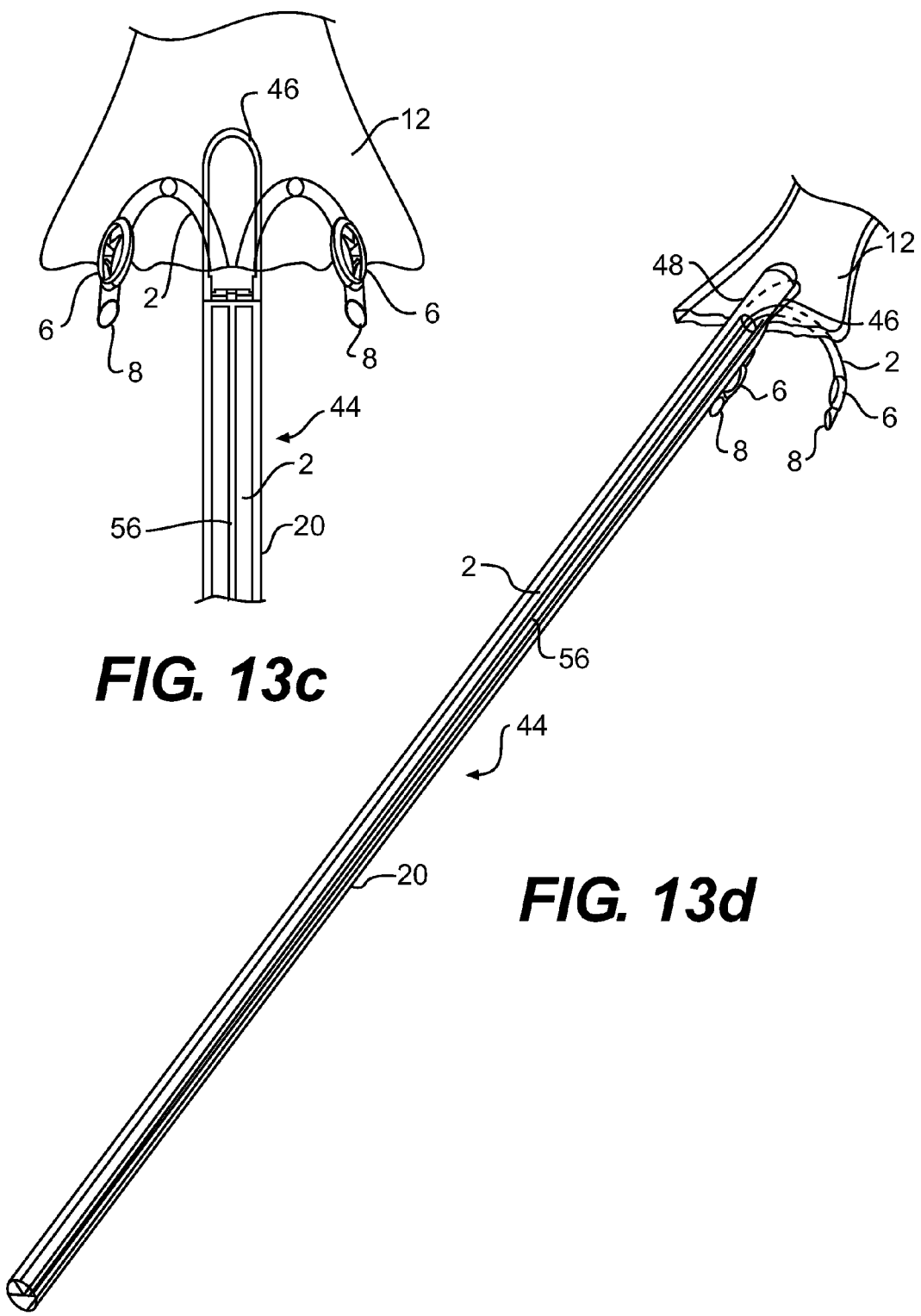

The grasping, suture passing device is inserted through the cannulae and the soft tissue is grasped at a desired location to pass the superelastic puncturing component, as shown in FIGS. 12a to c. At this point the superelastic puncturing component(s) can be threaded through the lumen(s) of the grasping, suture passing device such that it/they return(s) towards its/their preshaped geometry and pass(es) through the rotator cuff as it/they deflect(s) through the opening in the upper jaw of the grasping device. In the embodiment shown in FIGS. 12a to c, and FIGS. 13a to d, the grasping suture passing device incorporates two lumens to house two superelastic puncturing devices and an open area in the upper jaw 46 for the superelastic puncturing devices to pass through clamped soft tissue at predefined locations with specific spacing. The upper jaw 46 preferably overlaps the lower jaw 48 to define a larger opening so the superelastic puncturing devices can be separated by a larger spacing. The superelastic puncturing component is advanced enough to pass the suture fully into and through the opening of the upper jaw 46 of the grasping, suture passing device. Once the keyhole 6 containing the suture strand(s) is passed through the soft tissue 12, the suture is grabbed with a separate forceps or other mechanism and is pulled through the cannulae to facilitate tying the suture strands into mattress knots. The superelastic suture passing device is then withdrawn through the cannulae.

The embodiment shown in FIGS. 12a to c and FIGS. 13a to d incorporates two superelastic puncturing components therefore, both suture strands 16 required to create a mattress suture knot can be advanced through tissue simultaneously. However, if the grasping suture passing device only incorporates a single superelastic puncturing device, then the steps above can be repeated for positioning the other strand (limb) of the suture to enable creating a mattress suture concept.

The grasping suture passing device 44 shown in FIGS. 12a to c and FIGS. 13a to d incorporates an upper jaw 46 that pivots relative to the lower jaw 48. Pins locking the upper jaw to the lower jaw enable rotation of the upper jaw relative to the lower jaw. A stylette 56 is connected to the upper jaw at a location spaced radially from the upper jaw pivot point to cause the upper jaw to pivot as the stylette is retracted or advanced. The attachment between the upper jaw radial link and the stylette 56 also incorporates a pin to enable rotation of the stylette relative to the upper jaw radial link facilitating movement of the upper jaw as the stylette is actuated. The handle mechanism used to actuate the stylette, thus the upper jaw, and/or the superelastic puncturing components, can be a scissors type handle characteristic of a Rongeur device, a locking or non-locking forceps type handle characteristic of Castro Needle Drivers, an axial pusher such as that for tonsil snares, or other mechansism capable of independently or simultaneously actuating these components. If the handle mechanism is intended to simultaneously actuate the stylette and the superelastic puncturing components, predetermined delays in the actuation of these components can be achieved by incorporating axial slots that the handle mechanism passes links through and springs that determine the engagement location of the links to the components. These approaches and similar type mechanisms permit actuating the upper jaw prior to advancing the superelastic puncturing components and maintain clamping pressure on the soft tissue as the superelastic puncturing components can be advanced through the soft tissue. The mechanism reverses as the handle is released by retracting the superelastic puncturing components prior to releasing the soft tissue with the upper jaw.

An alternative approach, as shown in FIGS. 9c and d, involves the use of a grasping, suture passing device that has superelastic puncturing component(s) with at least one crochet hook 34, as opposed to the keyhole (as shown in FIGS. 13a to d). Once the superelastic puncturing component is advanced through the soft tissue, the crochet hook(s) is manipulated into engagement with at least one strand of suture 16 and is used to retract it into the lumen of the grasping, suture passing device such that it can be pulled outside the cannulae and tied into a knot with another strand, which can also be pulled through the soft tissue thus creating a mattress suture knot.

Figure 14A:
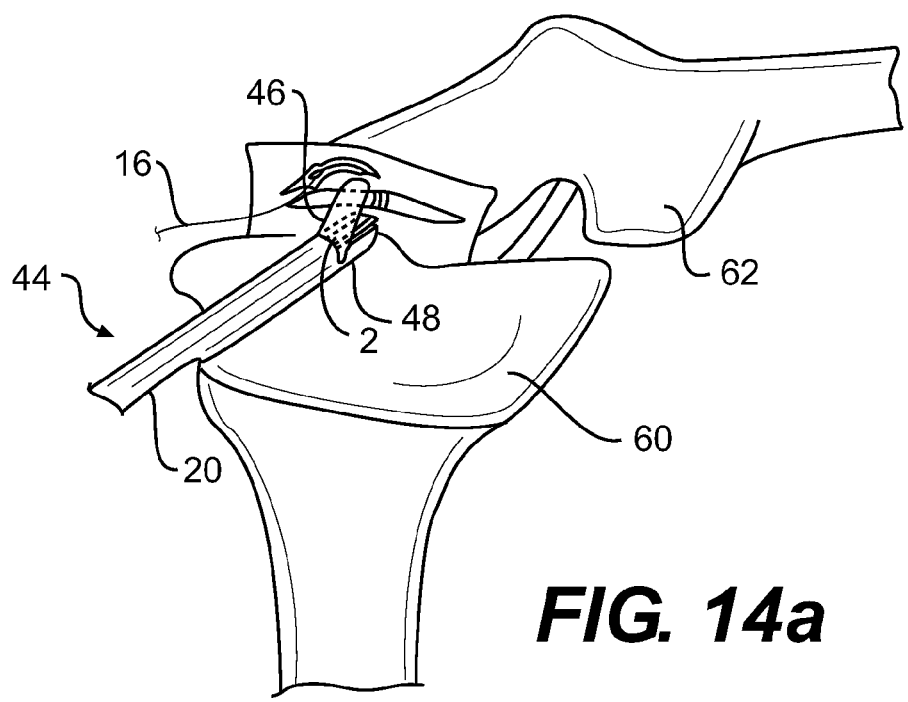
FIGS. 14a and b show perspective views of two grasping, suture passing device embodiments capable of positioning at least one suture strand for meniscus repair.
Figure 14B:
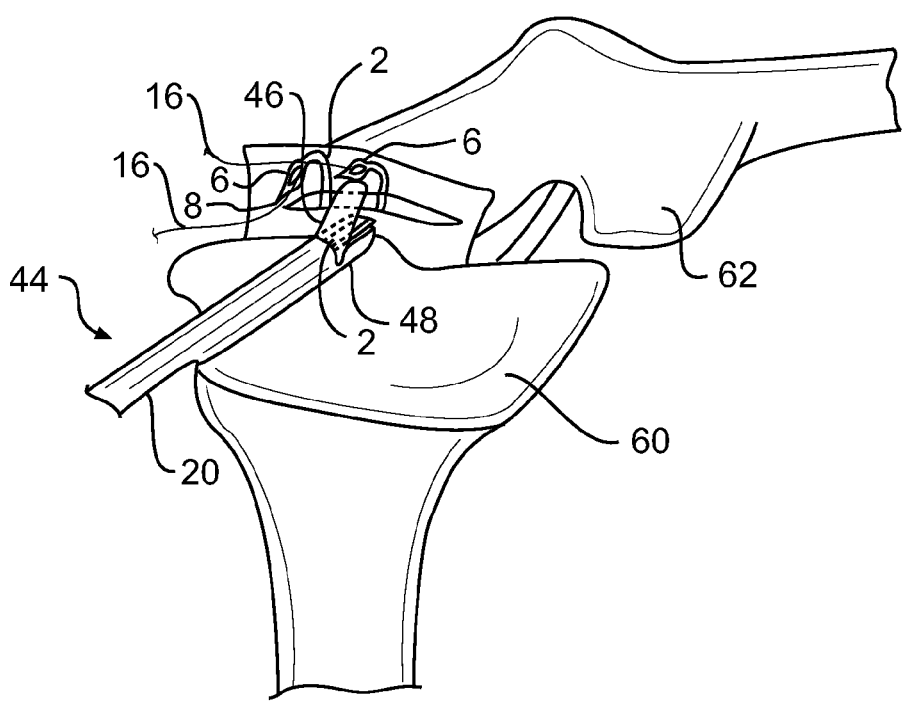

FIGS. 14a and b show approaches to repair meniscal tears involving the grasping, suture passing devices of the invention. The grasping, suture passing devices 44 engage the meniscus about the torn region of the soft tissue and advances the superelastic puncturing components such that they penetrate the meniscus on each side of the tear. The curvature of each superelastic puncturing component is chosen such that it punctures from one side of the tear through tissue and back up through the other side of the tear. This enables closing the tear as the suture strands can be tied into a knot. The grasping, suture passing device in FIGS. 14a and b advances two superelastic puncturing components thus two strands of suture through the meniscus about the meniscal tear. FIGS. 14a and b utilizes the grasping, suture passing devices of FIGS. 12a to c and FIGS. 13a to d as described above.

The suture passing device embodiments described above can be capable of creating other complex knots. By coordinating the movements of one or more superelastic puncturing components, these suture passing device embodiments can be able to place at least one suture strand through soft tissue such that the path the suture strand(s) follows through the soft tissue produces a complex knot once the suture strand(s) can be tied. For example, a FIG. eight knot can be created by passing a single suture strand through the keyholes of two puncturing components and passing the components through soft tissue such that they can be angled inward relative to each other and cause the suture strand ends to criss-cross once they are advanced or retracted through soft tissue. Once positioned, the free ends of the suture strand can be pulled from the keyhole (or crochet hook for embodiments that fish for the suture strand and pull it through soft tissue) and tied together thereby producing a figure eight knot. This same suture passing device can further be used to pass the free ends of the positioned suture strands through the soft tissue another time to further complicate the knot and increase the pull force and reliability of the knot, once tied. Other knots involving one or more passes of suture strands through the soft tissue can be created with the suture passing device embodiments of the invention (involving one or more superelastic puncturing components) by enabling passing the suture strands any number of times and at any position through the soft tissue.

Figure 15:
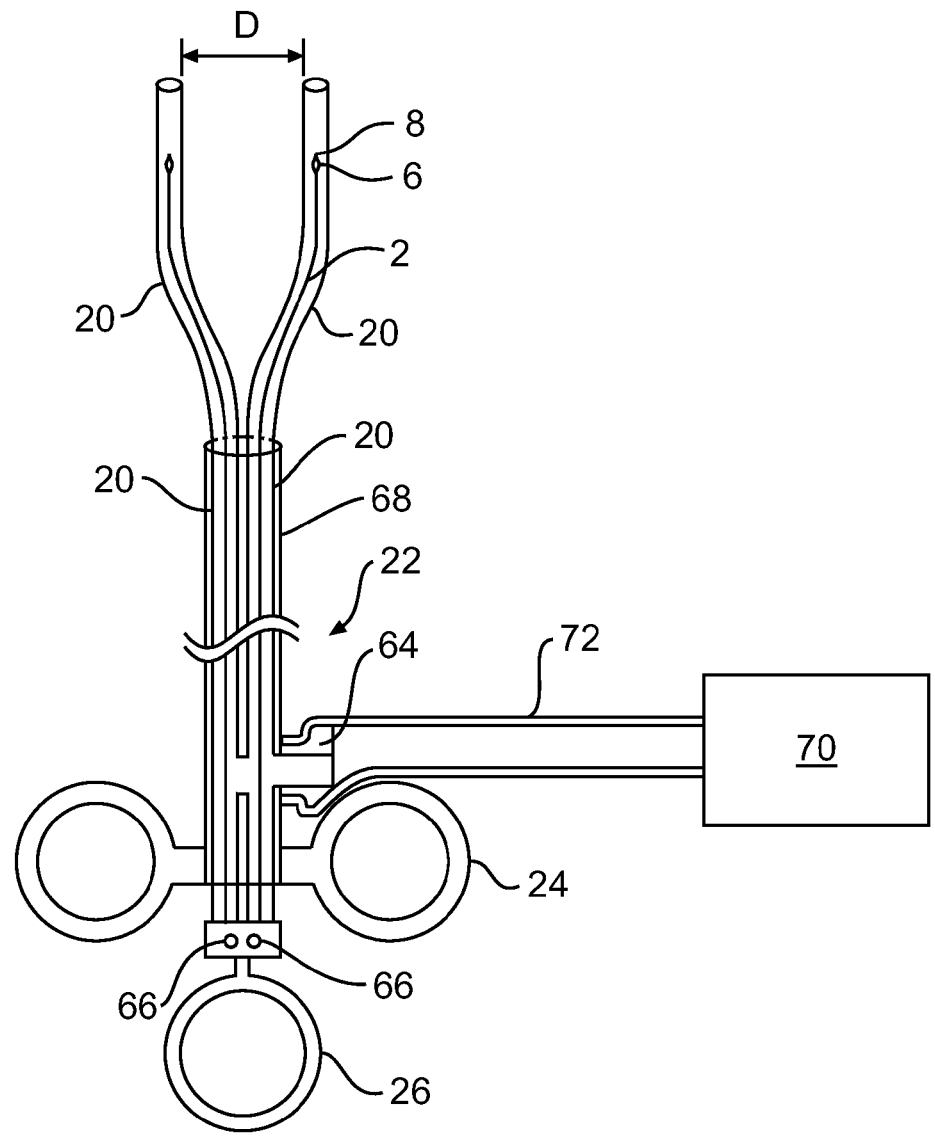
FIG. 15 shows a perspective view of another double barrel, grasping, suture passing device embodiment that incorporates at least two superelastic puncturing components to grab soft tissue through the use of suction.

An alternative grasping, suture passing device incorporates a suction mechanism instead of the clamping mechanism described above. FIG. 15 shows a double barrel suture passing device incorporating the straightening tubes separated by a distance, D, of at least 3 mm and preferably 5 mm, and a vacuum source 70 attached to a suction port 64 which is routed to the straightening tubes 20 thereby producing a suction at the ends of the straightening tubes to grasp tissue at the openings and maintain the tissue against the openings as the superelastic puncturing components 2 can be advanced through the soft tissue using the handle mechanism. The handle mechanism incorporates valves to permit actuation of the superelastic puncturing components without hindering the suction forces applied by the vacuum source 70.

The properties of the superelastic puncturing components, snares, and anchors described above can be varied to address applications in which the stiffness or elasticity needs to be varied accordingly. The composition of the superelastic material can be chosen to select the temperature range in which the needles, snares, or anchors exhibit stress-induced martensite. As such, the amount of austenite, and stress-induced martensite characteristics throughout a specific temperature range can be chosen to specify the degree of deflection and amount of force exerted by the superelastic puncturing components, snares, or anchors once deflected. For example, the superelastic properties of the material can be chosen so as the device is inserted into body and is exposed to an increase in environmental temperature, the associated temperature increase induces a change in the superelastic properties to provide, for example, increased rigidity and/or elasticity of the material.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims of the invention.

What is claimed is:

1. A surgical device for passing suture through soft tissue comprising:
    a cylindrical body having a lumen;
    an elongate member positioned substantially within and slideable through the lumen of the body, the elongate member including a distal portion having superelastic properties, the distal portion further including a transverse opening for carrying a suture therein, and wherein the suture is positionable completely outside of the lumen of the cylindrical body;
    a first jaw and a second jaw connected to the body and encompassing at least a portion of the elongate member, one of the jaws moveable relative to the other and having an opening, which is substantially transverse to a long axis of the moveable jaw, for allowing the distal portion of the elongate member therethrough and to the soft tissue; and
    a puncturing projection at the most distal end of the distal portion of the elongate member and slideable through the lumen of the body, the puncturing projection movable between a first position wherein the distal portion of the elongate member is in a substantially straight stressed configuration substantially contained within the lumen of the cylindrical body and between the first jaw and the second jaw and a second position wherein the distal portion of the elongate member is in a substantially curved unstressed configuration and extendable distally through and beyond the opening in the first jaw such that the opening in the distal portion carrying the strand of suture is positioned completely outside of the first jaw and the second jaw.

2. The device of claim 1, wherein said opening in said jaw extends through a middle region of said jaw such that said jaw is removable from around a side of a strand of suture that has been passed into the soft tissue.

3. The device of claim 1, wherein said opening in said distal portion of the elongate member comprises an eyelet.

4. The device of claim 1, further comprising a handle to manipulate movement of the jaws.

5. The device of claim 1, wherein the transverse opening in the elongate member comprises a flexible, closed-loop eyelet.

6. The device of claim 1, wherein the elongate member is substantially non-hollow.

* * * * *